United States Patent
Tai et al.

(10) Patent No.: US 12,318,627 B2
(45) Date of Patent: Jun. 3, 2025

(54) CONTROLLABLE OCULAR PHOTOTHERAPY

(71) Applicant: California Institute of Technology, Pasadena, CA (US)

(72) Inventors: Yu-Chong Tai, Pasadena, CA (US); Colin A. Cook, Monrovia, CA (US)

(73) Assignee: California Institute of Technology, Pasadena, CA (US)

(*) Notice: Subject to any disclaimer, the term of this patent is extended or adjusted under 35 U.S.C. 154(b) by 344 days.

(21) Appl. No.: 17/863,344

(22) Filed: Jul. 12, 2022

(65) Prior Publication Data

US 2022/0339464 A1 Oct. 27, 2022

Related U.S. Application Data

(62) Division of application No. 16/262,565, filed on Jan. 30, 2019, now Pat. No. 11,400,307.

(Continued)

(51) Int. Cl.
*A61N 5/06* (2006.01)
*A61B 5/297* (2021.01)

(52) U.S. Cl.
CPC ............ *A61N 5/0613* (2013.01); *A61B 5/297* (2021.01); *A61N 2005/0627* (2013.01);

(Continued)

(58) Field of Classification Search
CPC .............. A61N 5/06; A61N 5/0613; A61N 2005/0626; A61N 2005/0627;

(Continued)

(56) References Cited

U.S. PATENT DOCUMENTS

| 4,858,609 A | 8/1989 | Cole |
| 5,092,669 A * | 3/1992 | Anderson ............ G02C 5/001 |
| | | 351/203 |

(Continued)

FOREIGN PATENT DOCUMENTS

| CN | 102283742 A | 12/2011 |
| CN | 102413874 A | 4/2012 |

(Continued)

OTHER PUBLICATIONS

Arden et al., "A Preliminary Trial to Determine Whether Prevention of Dark Adaptation Affects the Course of Early Diabetic Retinopathy", Eye, vol. 24, No. 7, Jul. 2010, pp. 1149-1155.

(Continued)

*Primary Examiner* — John R Downey
(74) *Attorney, Agent, or Firm* — Mark P. Mathison

(57) ABSTRACT

Embodiments of the present disclosure are directed to a wearable phototherapy eye device. In an example, phototherapy can be controlled by varying an emission property of light emitted from the wearable phototherapy eye device to a user eye. In particular, the wearable phototherapy eye device includes a light source oriented to emit the light towards the user eye. The wearable phototherapy eye device also includes controls, such as electrical, mechanical, and/or electro-mechanical controls, to vary the emission property of the light based on an emission target associated with a sleep phase.

20 Claims, 10 Drawing Sheets

Related U.S. Application Data

(60) Provisional application No. 62/624,463, filed on Jan. 31, 2018.

(52) U.S. Cl.
CPC ................. *A61N 2005/0648* (2013.01); *A61N 2005/0651* (2013.01); *A61N 2005/0662* (2013.01)

(58) Field of Classification Search
CPC .... A61N 2005/0632; A61N 2005/0643; A61N 2005/0645; A61N 2005/0647; A61N 2005/0648
USPC ...................................................... 607/88–91
See application file for complete search history.

(56) References Cited

U.S. PATENT DOCUMENTS

| | | | |
|---|---|---|---|
| 5,154,707 A * | 10/1992 | Rink ................. | B23K 26/0096 606/15 |
| 5,220,359 A | 6/1993 | Roffman | |
| 5,347,326 A | 9/1994 | Volk | |
| 6,514,193 B2 | 2/2003 | Kaplan | |
| 6,563,243 B2 | 5/2003 | Obara et al. | |
| 6,733,490 B1 | 5/2004 | Falsini et al. | |
| 8,580,163 B2 | 11/2013 | Biel et al. | |
| 8,583,243 B2 | 11/2013 | Williams et al. | |
| 8,764,185 B1 | 7/2014 | Biederman et al. | |
| 8,945,197 B1 | 2/2015 | Friend et al. | |
| 9,176,332 B1 | 11/2015 | Etzkorn et al. | |
| 10,512,534 B2 | 12/2019 | Tai et al. | |
| 11,253,352 B2 | 2/2022 | Tai et al. | |
| 11,400,307 B2 | 8/2022 | Tai et al. | |
| 2003/0035301 A1* | 2/2003 | Gardiner ............... | G01J 3/0232 362/583 |
| 2003/0130709 A1* | 7/2003 | D.C. ..................... | G01J 3/0229 607/94 |
| 2005/0157256 A1 | 7/2005 | Gotou et al. | |
| 2005/0278003 A1 | 12/2005 | Feldman | |
| 2006/0106435 A1* | 5/2006 | Fraval .................. | A61B 5/0059 607/88 |
| 2009/0227996 A1 | 9/2009 | Powell et al. | |
| 2010/0103368 A1 | 4/2010 | Amirparviz et al. | |
| 2011/0089586 A1 | 4/2011 | Biel et al. | |
| 2011/0125078 A1 | 5/2011 | Denison et al. | |
| 2011/0257712 A1* | 10/2011 | Wells ................... | A61B 5/6886 607/90 |
| 2012/0041520 A1 | 2/2012 | Colbaugh et al. | |
| 2012/0199995 A1 | 8/2012 | Pugh et al. | |
| 2012/0245449 A1 | 9/2012 | Williams et al. | |
| 2013/0053929 A1 | 2/2013 | Colbaugh | |
| 2013/0060306 A1 | 3/2013 | Colbauch | |
| 2013/0211389 A1 | 8/2013 | Chuck et al. | |
| 2013/0265507 A1 | 10/2013 | Ford et al. | |
| 2014/0277291 A1 | 9/2014 | Pugh et al. | |
| 2014/0379054 A1 | 12/2014 | Cooper et al. | |
| 2015/0273179 A1* | 10/2015 | Krueger ................. | G02C 11/00 600/27 |
| 2015/0282706 A1 | 10/2015 | Sullivan | |
| 2015/0362754 A1 | 12/2015 | Etzkorn et al. | |
| 2016/0008625 A1 | 1/2016 | Barclay et al. | |
| 2016/0067087 A1 | 3/2016 | Tedford et al. | |
| 2016/0073922 A1 | 3/2016 | Aguirre et al. | |
| 2016/0158486 A1 | 6/2016 | Colbaugh et al. | |
| 2016/0220841 A1 | 8/2016 | Hill et al. | |
| 2016/0268012 A1 | 9/2016 | Williams | |
| 2016/0270656 A1 | 9/2016 | Samec et al. | |
| 2016/0278622 A1 | 9/2016 | Klubben et al. | |
| 2016/0317834 A1 | 11/2016 | Kirk et al. | |
| 2017/0333729 A1 | 11/2017 | Olcese | |
| 2017/0354326 A1 | 12/2017 | Pugh et al. | |
| 2018/0092738 A1 | 4/2018 | Tai et al. | |
| 2018/0133507 A1* | 5/2018 | Malchano .......... | A61N 1/36092 |
| 2018/0264284 A1 | 9/2018 | Alvarez et al. | |
| 2020/0319479 A1 | 10/2020 | Hahn et al. | |

FOREIGN PATENT DOCUMENTS

| | | |
|---|---|---|
| CN | 102892464 A | 1/2013 |
| CN | 203750025 U | 8/2014 |
| CN | 104069588 A | 10/2014 |
| CN | 104323773 A | 2/2015 |
| CN | 104582635 A | 4/2015 |
| CN | 204699261 U | 10/2015 |
| CN | 105431201 A | 3/2016 |
| EP | 0654256 A1 | 5/1995 |
| EP | 2817065 B1 | 4/2017 |
| JP | 2011087609 A | 5/2011 |
| JP | 2012524592 A | 10/2012 |
| JP | 2012528648 A | 11/2012 |
| JP | 2014028141 A | 2/2014 |
| JP | 2016507299 A | 3/2016 |
| JP | 2018501919 A | 1/2018 |
| WO | 2005079716 A1 | 9/2005 |
| WO | 2010122434 A1 | 10/2010 |
| WO | 2011094758 A2 | 8/2011 |
| WO | 2011141842 A1 | 11/2011 |
| WO | 2015033114 A1 | 3/2015 |
| WO | 2018075229 A1 | 4/2018 |

OTHER PUBLICATIONS

Arden et al., "Does Dark Adaptation Exacerbate Diabetic Retinopathy? Evidence and a Linking Hypothesis", Vision Research, vol. 38, No. 11, Jun. 1998, pp. 1723-1729.
Arden et al., "Spare the Rod and Spoil the Eye", British Journal of Ophthalmology, vol. 89, No. 6, Jun. 2005, pp. 764-769.
Arden , "The Absence of Diabetic Retinopathy in Patients with Retinitis Pigmentosa: Implications for Pathophysiology and Possible Treatment", The British Journal of Ophthalmology, vol. 85, No. 3, Mar. 2001, pp. 366-370.
Cameron et al., "Dark Adaptation of Human Rod Bipolar Cells Measured from the b-Wave of the Scotopic Electroretinogram", Journal of Physiology, vol. 575, No. 2, Sep. 1, 2006, pp. 507-526.
EP17863217.0 , "Extended European Search Report", May 18, 2020, 9 pages.
EP19747350.7 , "Extended European Search Report", Feb. 3, 2022, 6 pages.
EP19747350.7 , "Partial Supplementary European Search Report", Nov. 2, 2021, 10 pages.
Okawa et al., "ATP Consumption by Mammalian Rod Photoreceptors in Darkness and in Light", Current Biology, vol. 18, No. 24, Dec. 23, 2008, pp. 1917-1921.
PCT/US2017/054746 , "International Preliminary Report on Patentability", Apr. 18, 2019, 9 pages.
PCT/US2017/054746 , "International Search Report and Written Opinion", Mar. 27, 2018, 10 pages.
PCT/US2019/015863 , "International Preliminary Report on Patentability", Aug. 13, 2020, 8 pages.
PCT/US2019/015863 , "International Search Report and Written Opinion", Jun. 7, 2019, 11 pages.
Roos , "Theoretical Estimation of Retinal Oxygenation During Retinal Artery Occlusion", Physiological Measurement, vol. 25, No. 6, Dec. 2004, pp. 1523-1532.
Thomas et al., "Light Adaptation and Dark Adaptation of Human Rod Photoreceptors Measured From the α-Wave of the Electroretinogram", Journal of Physiology, vol. 518, No. 2, Jul. 15, 1999, pp. 479-496.
Yun et al., "Recent Developments in Laser Treatment of Diabetic Retinopathy", Middle East African Journal of Ophthalmology, vol. 22, No. 2, Apr.-Jun. 2015, pp. 157-163.

* cited by examiner

CONTROLLABLE OCULAR PHOTOTHERAPY

CROSS-REFERENCES TO RELATED APPLICATIONS

This application is a divisional application of U.S. patent application Ser. No. 16/262,565, filed Jan. 30, 2019, which claims the benefit of U.S. Provisional Application No. 62/624,463, filed Jan. 31, 2018, which is hereby incorporated in its entirety for all purposes.

STATEMENT AS TO RIGHTS TO INVENTIONS MADE UNDER FEDERALLY SPONSORED RESEARCH AND DEVELOPMENT

Not Applicable

BACKGROUND

Diabetic retinopathy is a leading cause of blindness in working age adults, affecting over four million Americans and 130 million individuals worldwide. Within fifteen years of diabetes onset, virtually all diabetics will suffer from retinopathy. The etiology of the disease is a degradation of the microvasculature supply in the retina, due to elevated blood glucose levels, leading to oxygen deficiency and edema. In the proliferative phase of the disease, retinal hypoxia drives the overexpression of angiogenic factors, notably vascular endothelial growth factor (VEGF), which induces aberrant neovascularization of the retina with often poorly formed and leaky vessels. The newly forming vessels lead to retinal bleeding, scarring, edema, and visual obstruction.

Many therapies for diabetic retinopathy are invasive and reactive in nature, including intravitreal anti-VEGF injections which block the angiogenic signaling cascade and panretinal photocoagulation which involves an array of laser burns across the peripheral retina to seal leaky vessels and reduce metabolic demand of the outer retina by approximately twenty percent. Due to the invasive nature of these interventions, patients often delay treatment until significant vision loss has occurred.

Non-invasive and preventative therapies for diabetic retinopathy are also available to mitigate disease progression in diabetics. The success of such a therapy may be found in a long-known property of the visual system: namely that retinal oxygen consumption is highest in the dark. It has been hypothesized that the increased retinal metabolism at nighttime exacerbates retinal hypoxia in diabetics and drives disease progression. This effect arises from the phototransduction pathway wherein the absorption of a photon ultimately leads to the closure of a number of sodium channels in the photoreceptor outer segment (i.e., open in dark, closed in light), with subsequent cell hyperpolarization and glutamate release. To maintain homeostasis, the sodium entering the outer segment channels is continuously pumped out from the inner segment. This circulating sodium current (a.k.a., dark current) requires the vast majority of rod energy expenditure to maintain and is inversely proportional to the logarithm of photon absorption. At an illumination resulting in 100-200 absorption events per second per rod, the energy expenditure of the rod is nearly halved.

The use of light to modulate retinal metabolism and oxygenation, henceforth referred to as phototherapy, represents an exciting preventative measure for diabetic retinopathy by mitigating hypoxia and subsequent VEGF expression. Researchers and companies have produced light-emitting sleep masks to deliver phototherapy through the closed eyelid to patients and have demonstrated promising therapeutic value in initial trials, with larger scale trials underway. Unfortunately, the sleep mask approach has suffered significantly from issues of patient compliance and treatment efficiency. In particular, trials have shown that over twenty-four percent of patients dropped out, and seventy-five percent reported adverse effects, primarily related to disturbed sleep. In terms of treatment efficiency, the dosage of the produced light reaching the retina varies significantly between patients and even per patient dependent on the sleep mask usages.

BRIEF SUMMARY

Embodiments of the present disclosure are directed to controllable ocular phototherapy, which overcomes challenges of compliance and dosage to make ocular phototherapy more effective and appealing. In various embodiments, a wearable phototherapy eye device is described. The wearable phototherapy eye device includes a facial housing having a user eye side. The wearable phototherapy eye device also includes a light source disposed in or on the facial housing and configured to emit light towards or from the user eye side. In addition, the wearable phototherapy eye device includes a controller electrically coupled with the light source and configured to vary an emission property of the light based on an emission target associated with a sleep phase of at least two sleep phases. Emission targets of the at least two sleep phases are different from each other and different from a zero emission.

In an example, the emission property is varied further based on a predetermined transfer function of the light from the wearable phototherapy eye device to an eye retina. For instance, the wearable phototherapy eye device further includes a set of electrodes configured to measure an electroretinogram (ERG) response of the eye retina at different light emission levels. The predetermined transfer function is defined based on the ERG response. Alternatively or additionally, the wearable phototherapy eye device further includes a set of electrodes configured to measure an electrooculogram (EOG) response of the eye retina at different light emission levels. The predetermined transfer function is defined based on the EOG response. In addition, the predetermined transfer function is defined based on the ERG response and the EOG response. The emission property of the light is varied to maintain the emission target at one of the different light emission levels during the sleep phase.

In an example, the wearable phototherapy eye device further includes a set of electrodes configured to measure an electrical response of the eye retina at different light emission levels. The predetermined transfer function is defined based on the electrical response and on transmissivity levels of an eye lid at the different emission levels.

In an example, the wearable phototherapy eye device further includes a receiving coil configured to induce electrical current based on a wireless power transmission from a transmission coil and a converter configured to convert the induced electrical current into a converted electrical current. Power to the controller is available based on the converted electrical current. In this example, the wearable phototherapy eye device further includes an energy storage electrically coupled with the converter and the controller and configured to supply the power to the controller.

In an example, the wearable phototherapy eye device further includes a set of sensors configured to measure data associated with at least one of a wear time of the wearable phototherapy eye device, a motion of the facial housing, or a user motion and a transceiver configured to transmit the data to a computing device and receive a setting of the emission property from the computing device. The setting is received based on a determination by the computing device of the sleep phase in response to the data. Additionally or alternatively, the emission property is determined by the controller further based on the data.

In other embodiments, a wearable phototherapy eye device is also described. The wearable phototherapy eye device includes a facial housing having a user eye side. The wearable phototherapy eye device also includes a radioluminescent light source disposed in or on the facial housing configured to emit radioluminescent light towards or from the user eye side. In addition, the wearable phototherapy eye device includes a shutter including a low light transmissivity portion having transmissivity relative to the radioluminescent light below a transmissivity level. The shutter is configured to vary an emission property of the radioluminescent light based on a relative position between the low light transmissivity portion and the radioluminescent light source.

In an example, the light source includes a cylindrical housing that has a transparent portion. The shutter includes a tubular housing that has an opaque portion corresponding to the low light transmissivity portion. The cylindrical housing is disposed inside the tubular housing. The emission property is varied based on a rotational movement of at least one of the cylindrical housing or the tubular housing such that the relative position between the transparent portion and the opaque portion is changed.

In an example, the light source includes a prismatic housing that has a transparent portion. The shutter includes an enclosure that has an opaque portion corresponding to the low light transmissivity portion. The emission property is varied based on a translational movement of at least one of the prismatic housing relative to the enclosure or the enclosure relative to the prismatic housing such that the relative position between the transparent portion and the opaque portion is changed.

In an example, the light source includes a housing that has a first pattern of transparent gratings and opaque gratings. The shutter includes an enclosure that has a second pattern of transparent gratings and opaque gratings. The emission property is varied based on at least one of a translational movement or a rotational movement of at least one of the housing or the enclosure such that the relative position between the first pattern and the second pattern is changed.

In an example, the light source includes a cylindrical housing that has a transparent portion. The shutter includes a hemi-circular housing that has an opaque portion corresponding to the low light transmissivity portion. The emission property is varied based on a rotational movement of the hemi-circular housing relative to the cylindrical housing such that the relative position between the transparent portion and the opaque portion is changed.

In an example, the shutter includes a reservoir and a transparent channel that is positioned between the radioluminescent light source and the user side. The reservoir includes a ferrofluid. The emission property is varied based on an amount of the ferrofluid in the transparent channel from the reservoir.

In an example, the shutter includes an optical waveguide that has an opaque gate. The emission property is varied based on a movement of the opaque gate.

In an example, the emission property is varied further based on a predetermined transfer function of the light from the wearable phototherapy eye device to an eye retina. In this example, the wearable phototherapy eye device further includes set of electrodes configured to measure an electrical response of the eye retina at different light emission levels. The predetermined transfer function is defined based on the electrical response.

In an example, the wearable phototherapy eye device further includes a receiving coil configured to induce electrical current based on a wireless power transmission from a transmission coil and a converter configured to convert the induced electrical current into a converted electrical current. In this example, the wearable phototherapy eye device also includes a controller electrically coupled with the shutter and configured to vary the relative position between the low light transmissivity portion and the radioluminescent light source and an energy storage electrically coupled with the converter and the controller and configured to supply power to the controller. In addition, the wearable phototherapy eye device includes a set of sensors configured to measure data associated with at least one of a wear time of the wearable phototherapy eye device, a motion of the facial housing, or a user motion, wherein the relative position is varied by the controller based on the data. Further, the wearable phototherapy eye device includes a transceiver configured to transmit the data to a computing device and receive a setting of the emission property from the computing device. The setting is received based on a determination by the computing device of the sleep phase in response to the data.

In other embodiments, a wearable phototherapy eye device is also described. The wearable phototherapy eye includes a phototherapy lens. This lens includes a lens body including a transparent optical zone and a periphery outside of the transparent optical zone. The lens body has a user side. The phototherapy lens also includes a light source disposed within the transparent optical zone or the periphery and configured to emit light towards the user eye side. Further, the phototherapy lens includes a controller disposed within the transparent optical zone or the periphery, electrically coupled with the light source, and configured to vary an emission property of the light. In addition, the phototherapy lens includes a receiving coil disposed within the periphery and configured to induce electrical current based on a wireless power transmission from a transmission coil and a converter disposed within the transparent optical zone or the periphery and configured to convert the induced electrical current into a converted electrical current. Power to the controller is available based on the converted electrical current.

In an example, the transparent optical zone has a circular shape defined by a radius of at least 3.5 mm, and wherein the light source is positioned within an inner circle of the circular shape having a radius of less than 2 mm. For instance, a light source is positioned about the center of the circular shape. The controller and converter are disposed within the periphery.

In an example, the light source includes a light emitting diode. A side of the light emitting diode opposite to the user side is opaque to the light. The lens body includes a first lens, a second lens, and a gap. The light source is disposed within the gap. The gap includes an oxygen permeable material and is uniformly distributed within the lens body. The light source includes a coating of an oxygen permeable material. Each of the first lens and the second lens has a thickness between 10 and 100 µm. The gap separates the first lens and the second lens by a separation between 100 µm and 1 mm.

In an example, the first lens is made of an optical material of a first type and the second lens is made of an optical material of a second type. The first type and the second type are different. For instance, the first lens is an optical correction lens made with silicone material and the second lens is a rigid gas permeable (RGP) contact lens.

In an example, the first lens has a first curvature and the second lens has a second curvature different from the first curvature. Outer peripheries of the first lens and the second lens mate at the periphery of the lens body. The gap is defined based on the first curvature and the second curvature.

In an example, the controller is configured to vary the emission property of the light based on an emission target associated with a sleep phase. The emission property is varied further based on a predetermined transfer function of the light from the phototherapy lens to an eye retina. The phototherapy lens further includes a set of electrodes configured to measure an electroretinogram (ERG) response of the eye retina at different light emission levels. The predetermined transfer function is defined based on the ERG response.

In other embodiments, phototherapy kit is also described. The phototherapy kit includes a phototherapy eye device that includes at least one of a wearable phototherapy eye device or a phototherapy lens. The phototherapy kit also includes a pupil constriction preventing agent that comprises at least one of parasympatholyticss, anticholinergic mydriatics, or sympathomimetics.

A further understanding of the nature and the advantages of the embodiments disclosed and suggested herein may be realized by reference to the remaining portions of the specification and the attached drawings.

DETAILED DESCRIPTION

Figure 1:
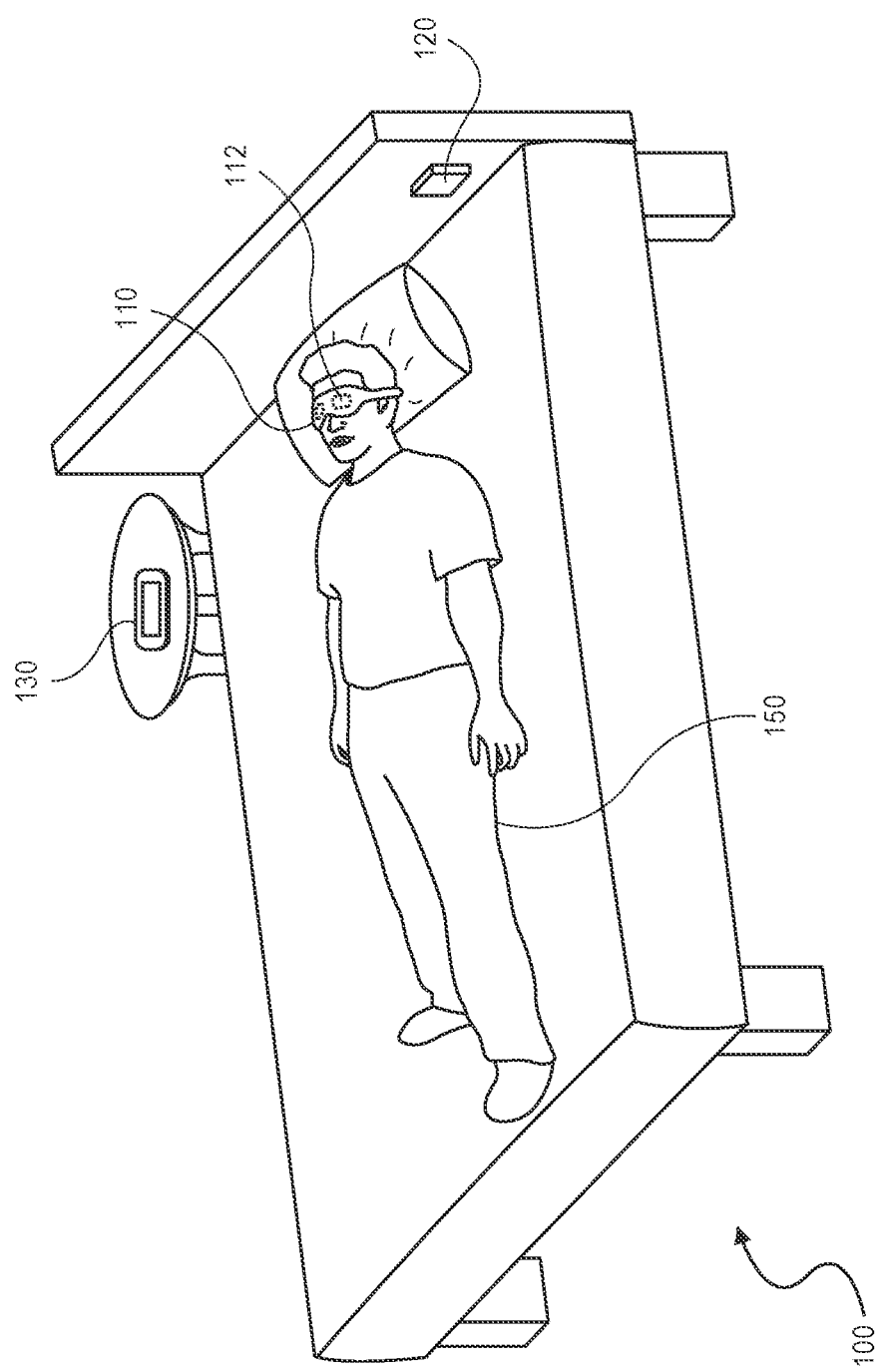
FIG. 1 illustrates an example of a phototherapy eye system, according to embodiments of the present disclosure.

Embodiments of the present disclosure are directed to controllable ocular phototherapy, which overcomes challenges of compliance and dosage to make ocular phototherapy more effective and appealing. Generally, a phototherapy eye device is used to controllably emit light, where an emission property of the light is varied based on an emission target associated with a sleep phase. For example, during an initial sleep phase, the light emission may be ramped up until a second phase sleep is entered. During this second phase, the emitted light has, at peak emission, a wavelength between 400 nm and 600 nm ($1.57 \times 10^{-5}$ inch to $2.36 \times 10^{-5}$ inch) and produces an irradiance on the retina of substantially $10^9$ to $10^{11}$ photons/s/cm². Thereafter, the light emission is ramped down during a third sleep phase, before being turned off at the end of this phase.

The phototherapy eye device may be a wearable device. Different types of wearable devices are possible. In one example, the wearable device is a facial mask that a user can attach to their face. The facial mask includes at least one light source for each eye and controls to vary the emission property (e.g., irradiance, intensity, wavelength, etc.). The controls may depend on the type of the light source. For instance, the light source can include one or more light emitting diodes, where the supply of electrical power to the diode(s) can be controlled. In another illustration, the light source can include a radioluminescent light source and the controls can include shutters that vary the amount by which a light-transparent portion of the light source is exposed to the eye. In another example, the wearable device is a phototherapy lens that includes a light source and controls. The phototherapy lens can be implemented as a contact lens, where the light source is placed in a transparent optical zone of the contact lens corresponding to a pupil. Alternatively, the phototherapy lens can be implemented as an intraocular lens implantable inside the eyeball.

Depending on the specific type of light source and/or type of controls, electrical power may be supplied to the wearable device. In an example, the wearable device is passive and is powered wirelessly from a remote power source when in physical proximity to this source. In another example, the wearable device includes an energy storage, such as a high capacitance battery, and is rechargeable via wireless power transmission. In yet another example, the wearable device includes a replaceable energy storage.

To increase the efficiency of the phototherapy, target emissions may be set for different sleep phases, where emission targets of at least two sleep phases are different from each other and different from a zero emission. For instance, and referring back to the three sleep phase example above, the light emitted during the second phase has the highest emission radiance, whereas this radiance is smaller in the first and third phases. The number and duration of sleep phases and the target emission per sleep phase can be personalized to the user.

In addition, the efficiency can be increased by accounting for a predetermined transfer function of the light from the wearable device to the eye retina when controlling the light emission in each sleep phase or in particular one or more sleep phases. More specifically, the transmissivity of the light path may be impacted by different factors such as the light transmissivity of the eye lid (in the case of a facial mask), the electroretinogram (ERG) response of the eye retina, and/or the gaze angle of the eye. Eye lid transmissivity measurements, ERG measurements, and/or electroculogram (EOG) measurements may be performed to derive the transfer function for the user. In an example, these measurements can be performed by a measurement system(s) different from the wearable device. In another example, the wearable device can include the relevant components to perform these measurements and derive, in real-time during the different sleep phases, the transfer function.

To illustrate, the wearable device includes a light sensor. Light is emitted from a light source of the wearable device at different emission levels with the eye lid shut. Light reflected from the eye lid at the different transmission levels is measured by the light source. The eye lid transmissivity can be derived as a function of the transmission levels based on differences between the emitted light and reflected light. For a desired emission target during a sleep phase, the emitted light is set at a transmission level that would achieve the desired emission target given the eye lid transmissivity.

Additionally or alternative, the wearable device includes a set of ERG electrodes. During a calibration period within a sleep phase having a target emission, light is emitted from the light source at the different emission levels and the ERG response is measured based on the ERG electrodes. The ERG response indicates the emission level that would result in the target emission. Accordingly, the emitted light is set at that particular emission level for the sleep phase.

Additionally or alternatively, the wearable device includes a set of EOG electrodes. During a sleep phase having a target emission, light is emitted and the EOG response is measured based on the EOG electrodes. The EOG response indicates a gaze angle of the eye. A correlation table is looked up for a correlation between the gaze angle and an emission level that would achieve the target emission. Accordingly, the emitted light is set at that particular emission level for the sleep phase.

The foregoing and other features of the phototherapy eye device are further described in connection with the next figures. There are several technical advantages of this phototherapy eye device, such as increasing the compliance and the efficiency of the dosage by controlling the emitted light during sleep phases dependently on the user.

FIG. 1 illustrates an example of a phototherapy eye system 100, according to embodiments of the present disclosure. As illustrated, the phototherapy eye system 100 includes a wearable phototherapy eye device 110, a power source 120, and a computing device 130. A user 150 may wear the wearable phototherapy eye device 110 for phototherapy treatment. The power source 120 may supply electrical power to the wearable phototherapy eye device 110. The computing device 130 may provide instructions and/or data controlling certain operations of the phototherapy eye device 110. Although FIG. 1 illustrates these components being separate from each other, some or all of the components can be integrated. For instance, the wearable phototherapy eye device 110 can include the power source 120 and/or the computing device 130.

In an example, the wearable phototherapy eye device 110 includes at least one light source 112 per eye of the user 150. Upon wearing the wearable phototherapy eye device 110, each light source 112 is positioned to be in proximity to and over the corresponding eye such that light emitted from the light source 112 propagates towards the eye. In particular, the light source 112 may be substantially centered relative to the pupil of the eye. The wearable phototherapy eye device 110 can be implemented as a facial mask, a helmet that extends over the user's 150 eyes, goggles, eye glasses, and/or other devices that can be worn by the user 150 and that can locate the light sources in proximity to and over the eyes. Further configuration examples of the wearable phototherapy eye device 110 are illustrated in connection with FIGS. 2-5.

The power source 120 can supply power to the wearable phototherapy eye device 110 using different means for power transmission. In an example, the power source 120 may provide wireless power transmission. In this example, the wearable phototherapy eye device 110 is passive when remote from the power source 120 and is activated only (e.g., powered up) when in physical proximity to the power source 120. Alternatively, the wearable phototherapy eye device 110 includes a high capacity energy storage, such as a high capacitance battery, that can be recharged when in physical proximity to the power source 120. A further configuration in this example of the power source 120 is illustrated in connection with FIG. 6. In another example, the power source 120 can include a power outlet, and power can be supplied to the wearable phototherapy eye device 110 using a safely detachable power cable. In yet another example, the power source 120 can be a replaceable or a rechargeable high capacity energy storage that is installed in the wearable phototherapy eye device 110.

The computing device 130 generally includes a memory storing computer-readable instructions and a processor suitable for execution of the instructions such that, upon execution, the computing device 130 can perform various programmed operations related to phototherapy. In an example, the computing device 130 may be a personal electronic device of the user 150, such as a smartphone or a tablet, or can be a desktop computer. In another example, the memory and the processor (or, similarly, an application-specific integrated circuit (ASIC) implemented for the phototherapy-related operations) can be integrated with the wearable phototherapy eye device 110.

Various types of phototherapy-related operations are possible on the computing device 130. In one example, the wearable phototherapy eye device 110 sends, wirelessly or via a wired data interface, data to the computing device 130. This data can include any of timestamps (e.g., current time), a wear time of the wearable phototherapy eye device 110, a motion of the wearable phototherapy eye device 110 (device motion), a motion of the user 150 (a user motion), a sleep phase, an emission target of the sleep phase, an emission property of the emitted light during the sleep phase (e.g., the irradiance, intensity, wavelength), ERG response, EOD response, eye lid transmissivity, and/or other phototherapy-related. In this example, the computing device 130 can be configured to monitor, track, and present information to the user 150 about the phototherapy.

In another example, the data sent to the computing device 130 includes only the timestamps, the wear time, the device motion, and/or the user motion. In comparison, the computing device 130 may store a user profile for the user 150, where this profile may identify target emissions per sleep phase given a predetermined transfer function. This function may be defined for the user based on ERG, EOG, and/or eye lid transmissivity measurements performed by one or more measurement systems operated by a health provider or physician. Based on the received data, the computing device 130 may determine the sleep phase and identify the relevant target emission. Thereafter, the computing device 130 may instruct the power source 120 to supply the proper amount of power to achieve the target emission and/or instruct a controller of the wearable phototherapy eye device 110 to vary the emission property of emitted light to achieve the target emission.

In yet another example, the controls can be distributed between the computing device 130 and the wearable phototherapy eye device 110. For example, the wearable phototherapy eye device 110 may determine the sleep phase based on the timestamps, the wear time, the device motion, and/or the user motion and may send an indication of the sleep phase to the computing device 130. In response, the computing device 130 can control the power source 120 and/or the wearable phototherapy eye device 110 to achieve the target emission.

Figure 2:
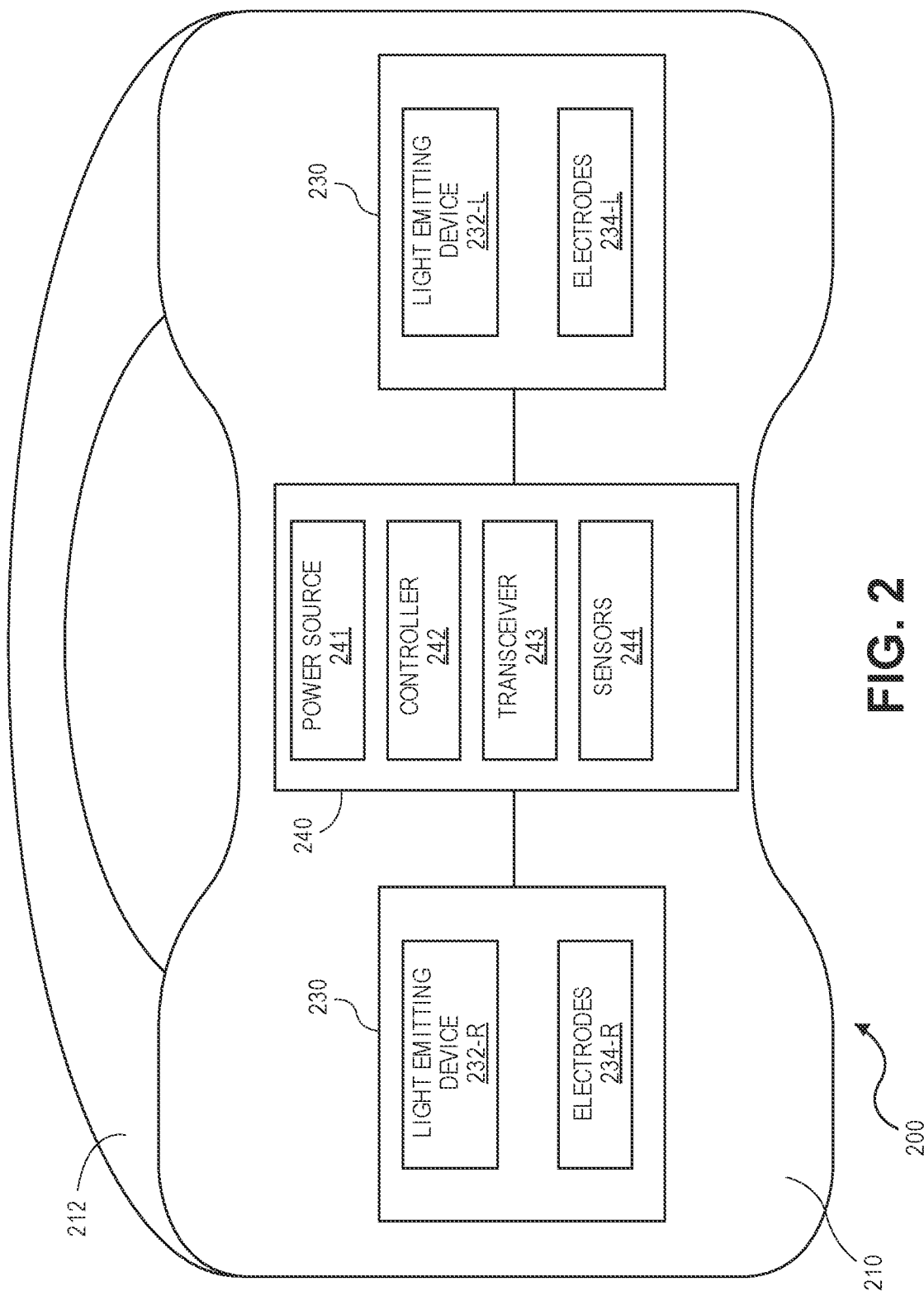
FIG. 2 illustrates an example of a wearable phototherapy eye device, according to embodiments of the present disclosure.

FIG. 2 illustrates an example of a wearable phototherapy eye device 200, according to embodiments of the present disclosure. As illustrated, the wearable phototherapy eye device 200 is a facial mask that is wearable by a user and that includes a body 210 and a strap 212. The body 210 includes a light source 230R, a light source 230L, and circuitry 240. In operation, the body 210 is worn on the user's face and the strap 212 surrounds the user's head. The light source 230R is positioned over the user's right eye (or at least a portion of this eye) and can be substantially centered with the right pupil. The light source 230L is positioned over the user's left eye (or at least a portion of this eye) and can be substantially centered with the left pupil. Components and controls of the two light sources are typically similar.

In the interest of avoiding redundant description, FIG. 2 is described herein next in connection with a light source 230 that represents either one of the light source 230R and light source 230L. In addition, although FIG. 2 illustrates that the circuitry 240 is common to both light sources 230R and 230L, similarly circuitry can be implemented per light source.

Generally, the body 210 represents a facial housing that can be mounted to or attached to the user's face. As illustrated in connection with FIG. 1, rather than using a facial mask, other devices are possible including a helmet, goggles, or eye glasses. In each of such example, the device includes a facial housing to position the light source 230 proximate to and over an eye. The facial housing, whether for the body 210 or for the other devices, includes a user eye side and an opposite side. In operation, the user eye side faces the eye, and the opposite side faces the surrounding physical environment of the user. The light source 230 disposed in or on the facial housing and is configured to emit light towards (if disposed in) or from (if disposed on) the user eye side.

In an example, the light source 230 is disposed in the body 210, such as in a channel, a pocket, or some other attachment means within the body 210. A transparent and protective layer of the body 210 may cover the light source 230 on the user side. Transparency is used herein to generally refer to a material having a transmissivity relative to the emitted light over a desired transmissivity level (e.g., the material has a ninety percent or more light transmissivity for a given range of wavelength). The light source 230 is oriented towards the user side such that emitted light propagates through the transparent and protective layer and to the eye. In another example, the light source 230 is disposed on the user side of the body 210 (e.g., attached externally on the exterior surface of the body 210 on the user side, where the attachment can be secure and includes stitching and/or gluing a periphery of the light source 230 to the exterior surface of the body 210). In this example, the light source 230 is also oriented such that the emitted light propagates and to the eye.

The light source 230 includes a light emitting device 232 (shown as device 232R for light source 230R and device 232L for light source 230L). Different configurations of the light emitting device 232 are also possible. For instance, the light emitting device 232 can include a set of at least one organic light emitting diode, a set of at least one electroluminescent emitter, a set of at least one light emitting cell, and/or a set of at least one light emitting electrochemical cell.

Optionally, the light source 230 also includes a set of electrodes 234 (shown as electrodes 234R for light source 230R and electrodes 234L for light source 230L) and/or light sensors (not shown) to measure an electrical response of the eye. For instance, the set of electrodes 234 can include any or a combination of a set of electroretinography electrodes for measuring an ERG response of the eye's retina, a set of electrooculography electrodes for measuring an EOG response of the retina, or a set of light sensors to measure the light transmissivity of the eye's lid. In the case of electroretinography electrodes, these electrodes can include DTL silver and/or nylon fiber strings, can be distributed uniformly around the light emitting device 232, and disposed on the exterior surface of the light source 230 on the user side to become as close as possible to the eye's cornea when the wearable phototherapy eye device 200 is in operation. In the case of electrooculography electrodes, these electrodes can be made out of brass and/or copper, can be disposed at known locations on the light source 230 on the user side such that, when a gaze angle is computed relative to the electrooculography electrodes, the gaze angle relative to the light emitting device 232 can be derived therefrom. For light sensors configured to measure the eye lid light transmissivity, these sensors can be positioned at locations on the light source 230, where these locations would be over the eye lid when the wearable phototherapy eye device 200 is in operation.

The circuitry 240 provides power and control to the light source 230. In an example, the circuitry includes a power source 241, a controller 242 and, optionally, a transceiver 243 and a set of sensors 244. Some or all of these components may be electrically coupled with the light source 230.

Different configurations of the power source 241 are possible, depending on whether the wearable phototherapy eye device 200 should be powered wirelessly or not and whether this device 200 should be passive or not. In an example of a wireless and passive device, the power source 241 includes a set of receiving coils and a set of converters (e.g., AC to DC converters and, optionally, DC to DC converters) among other components. The receiving coil is configured to induce electrical current based on a wireless power transmission from a transmission coil from a remote power source. The set of converters is configured to convert the induced electrical current into a converted electrical current. Power to the wearable phototherapy eye device 200, including to the controller 242, transceiver 243, sensors 244, and light source 230, is available based on the converted electrical current. The power source 241 may incorporate multiple receiving coils at orthogonal orientations to ensure efficient wireless power transfer regardless of how the user orients their head and, equivalently, the facial mask. Feedback on the orientation of the facial mask (e.g., based on a gyroscope of the sensors 244) may be used to determine the optimal coil(s) to use for the power reception. In addition, the receiving coils can be distributed within the body 210, within the strap 212, or within both the body 210 and the strap 212.

In an example of a wireless and active device, the power source 241 further includes a high capacity energy storage (e.g., a high capacitance battery) electrically coupled with the set of converters and with the controller 242, transceiver 243, sensors 244, and light source 230. The converted electrical current is supplied to and stored in high capacity energy storage for supply to the controller 242, transceiver 243, sensors 244, and light source 230. In an example of a wired device, the power source 241 may instead include a replaceable battery.

Different configurations of the controller 242 are also possible, depending on the type of controller effectuated by the controller 242 and/or any distribution of phototherapy-related operations between the wearable phototherapy eye device 200 and a remote computing device. In an example, the controller 242 can include a set of resistors, inductors, and capacitors that form with the power source 240 and RLC circuit that control the operations of a light emitting diode (as an example of the light emitting device 232). In another example, the controller 242 can further include a set of Zener diodes and other electronic components to vary an emission property of the light emitting diode (e.g., by varying the voltage and/or current to the light emitting diode, different irradiance levels are possible, each of which can be used for a sleep phase). In yet another example, the controller 242 can be implemented as an ASIC or a microprocessor (e.g., including a processor and a memory storing computer-readable instructions) to implement additional controls and data reporting, such as to derive a transfer function of the light from the wearable phototherapy eye device 200 to the retina based on measurements provided from the light source 230, to determine a sleep phase based on wear time, time of day, and data from the sensors 244, to maintain a profile of the user, and/or to receive and execute instructions from the remote computing device.

In an example, the transceiver 243 includes a receiver that receives instructions and/or data from the remote computing device and a transmitter that transmits instructions and/or data to the remote computing device. The transmitted data can include data processed by the controller 242, data measured by the electrodes 234 and/or light sensors, and data measured by the sensors 244. The instructions can be exchanged between the controller 242 and the remote computing device via the transceiver 243.

The sensors 244 are configured to provide measurements about a wear time of the wearable phototherapy eye device 200, device motion, and user motion. For instance, the sensors 244 includes a temperature sensor that detects the user's temperature and trigger a time clock, thereby indicating the wear time. The sensors 244 can also include a motion sensor to detect the device motion and a gyroscope that, in conjunction with the motion sensor, can detect the user motion.

In an example, the controller 242 is configured to control various phototherapy-related operations. The configuration can be implemented as specialized hardware or as computer-readable instructions stored in a memory for execution by a processor. The operations includes varying an emission property of the light emitted from the light source 230 (e.g., from the light emitting device 232) based on an emission target, where this target may be associated with a sleep phase. The emission property refers to a property of the emitted light that may impact the phototherapy and includes, for instance, any or a combination of irradiance, intensity, wavelength, emission time, emission pattern, and the like. An emission target refers to a targeted emission property, such as an amount of photons per second and per square centimeter, a particular wavelength, a particular amount of emission time, and the like. The controller 242 may vary the emission property at the start, end, and/or during the sleep phase to meet the emission target. Varying the emission may include changing, for instance, the electrical current and/or electrical voltage supplied to the light emitting device 232. Typically, the phototherapy is carried by emitting a light with a wavelength in the range of 400 nm to 600 nm and an irradiance in the range of $10^9$ to $10^{11}$ photons per second per $cm^2$ (photons/s/$cm^2$).

Generally, the user may be associated with a phototherapy profile that identifies one or more sleep phases and one or more emission targets per sleep phase. This profile may be personalized to the user and defined by the user or by a physician. The phototherapy profile can be accessible to the controller 242 locally or remotely (e.g., from the remote computing device). Upon a detection of a sleep phase, the controller 242 may determine the target emission for that sleep phase or may receive instructions about this target emission from the remote computing device. The sleep phase detection can be performed locally by the controller 242 based on the data collected by the sensors 244 or remotely by the remote computing device based on this data or other sleep-related data accessible to the remote computing device.

To increase the efficiency and effectiveness of the phototherapy, the phototherapy profile may store a predetermined transfer function of the light from the wearable phototherapy eye device 200 to the retina. This transfer function can be defined based on measurements of a remote measurement system, where the measurements can be specific to the user or can be across a wide user base. The measurements can include ERG measurements, EOG measurements, and/or eye lid light transmissivity measurements. Additionally or alternatively, the transfer function can be defined and/or updated over time based on similar measurements performed with the set of electrodes 234 and/or any light sensors. For instance, the controller 242 can trigger light emissions from the light emitting device 232 at different emission levels (e.g., wavelengths, irradiances, etc.) and receive the related measurements from the set of electrodes 234 and/or light sensors. Such measurements can be processed by the controller 242 that then generates and/or updates the transfer function, or can be sent to a remote computing device to then generate and/or update the transfer function.

The transfer function can be used to vary the emission property to meet the emission target. For instance, for a particular sleep phase where the eye lid is completely shut, the transfer function can indicate the eye lid light transmissivity (e.g., 50%). To meet the emission target (e.g., $10^{11}$ photons per second per $cm^2$ (photons/s/$cm^2$)), the emission property is adjusted given this transmissivity level (e.g., the irradiance is doubled to $2\times10^{11}$ photons/s/$cm^2$). Similarly, the transfer function can indicate a particular EOG response showing a half a peak at one of the irradiance levels for a particular wavelength. The emission property can be adjusted to correspond to the half-peak irradiance level and the wavelength.

In addition, the transfer function can be used to vary the emission property during the sleep phase. In particular, the eye may move (e.g., roll back), impacting the retinal exposure to the light (or, similarly, the light path from the light emitting device 232 to the retina). The transfer function can indicate an emission property to satisfy an emission target given a gaze angle of the eye. During the sleep phase, ERG measurements can be performed continuously or at time intervals (e.g., every one second, ten seconds, on minute, etc.) and indicate the gaze angle. These measurements can then be used to determine, from the transfer function, the emission property needed to satisfy the target emission for the sleep phase given the measured gaze angle. The light emitted from the light emitting device 232 can be adjusted to have the determined emission property.

Figure 3:
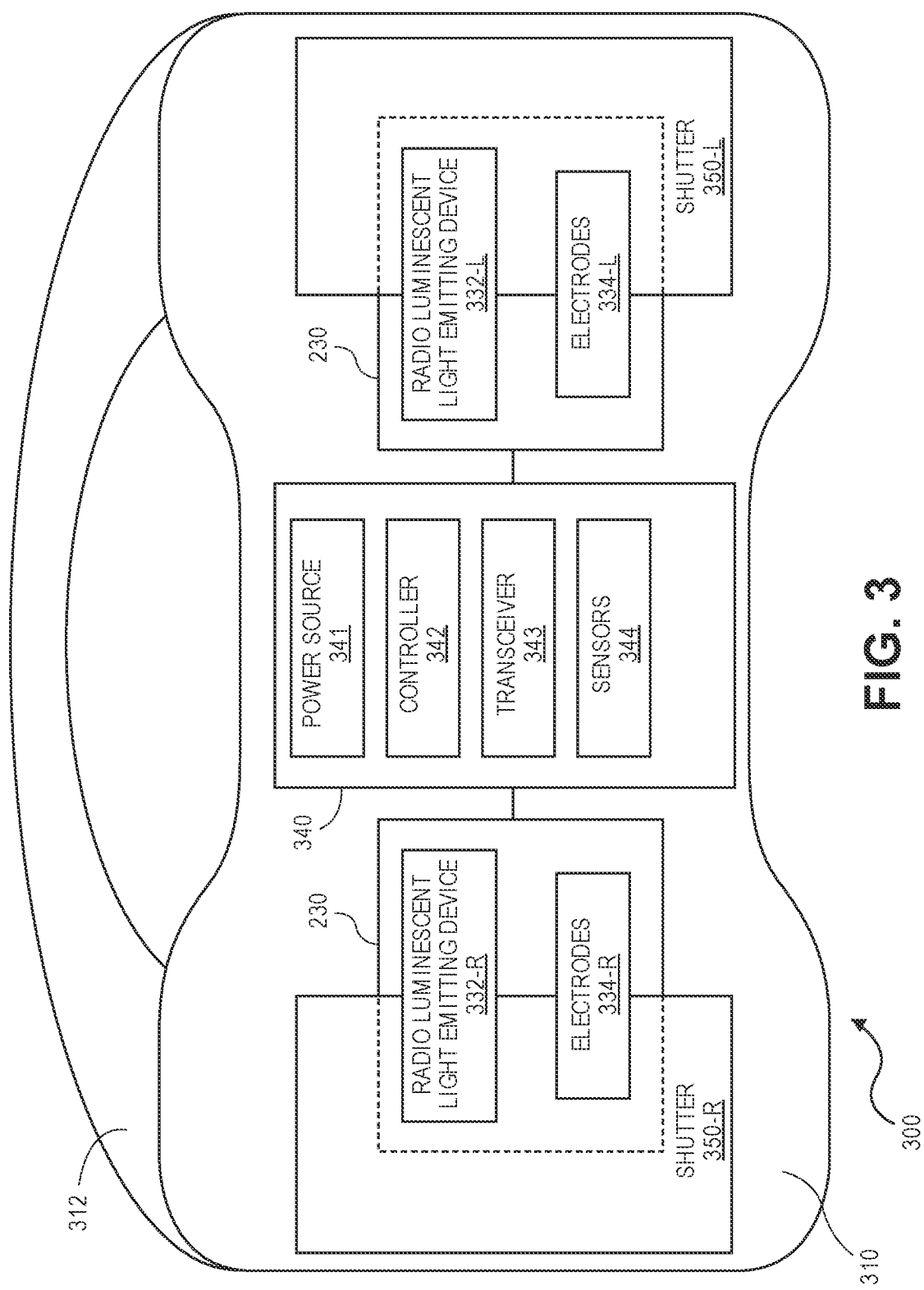
FIG. 3 illustrates another example of a wearable phototherapy eye device, according to embodiments of the present disclosure.

FIG. 3 illustrates another example of a wearable phototherapy eye device 300, according to embodiments of the present disclosure. In an example, rather than using a light emitting device that is electrically powered as in the wearable phototherapy eye device 200 of FIG. 2, the wearable phototherapy eye device 300 here uses a radioluminescent light emitting device. The use of radioluminescent light can provide an effective phototherapy with a simple design implementation. Controlling the phototherapy can also be achieved by using shutters that can control the emitted light.

Generally, the wearable phototherapy eye device 300 is a facial mask that is wearable by a user and that includes a body 310 and a strap 312, although other configurations are possible including a helmet, googles, and eye glasses. In operation, the body 310 is worn on the user's face and the strap 312 surrounds the user's head.

In a first example, the body 310 includes a radioluminescent light emitting device 332R and a radioluminescent light emitting device 332L, but no other phototherapy-related components. In this first example, the light emission is not controlled over time. In a second example, the body 310 and/or the strap 312 include other phototherapy-related components to provide controls over the light emitted from the radioluminescent light emitting devices 332R and 332L. These components include, for instance, circuitry 340, a set of electrodes 334-R, a set of electrodes 334-L, a set of shutters 350R, and a set of shutters 350L. In this second example, the light emission is controlled over time. In the interest of avoiding redundant description, FIG. 3 is described herein next in connection with a light source 330, a radioluminescent light emitting device 332, a set of electrodes 334, and a set of shutters 350 that represent, respectively, either one of the light source 330R and light source 330L, the radioluminescent light emitting device 332R or the radioluminescent light emitting device 332L, the set of electrodes 334R or the set of electrodes 334L, and the set of shutters 350R or the set of shutters 350L. In addition, although FIG. 3 illustrates that the circuitry 340 is common to both sets of electrodes 334R and 334L and to both sets of shutters 350R and 350L, similar circuitry can be implemented per set of electrodes and/or per set of shutters. The first example is described herein next first, followed by the second example.

In the first example, the wearable phototherapy eye device 300 includes the body 310, the strap 312, and the radioluminescent light emitting device 332 but not the circuitry 340, the set of electrodes 334, and the set of shutters 350. The body 310 is an example of a facial housing that has a user side and an opposite side. In operation, the user eye side faces the eye of the user, and the opposite side faces the surrounding physical environment of the user. The radioluminescent light emitting device 332 is disposed in or on the facial housing and is configured to emit light towards (if disposed in) or from (if disposed on) the user eye side.

In an example, the radioluminescent light emitting device 332 is disposed in the body 310. A transparent and protective layer of the body 310 may cover the radioluminescent light emitting device 332 on the user side. The radioluminescent light emitting device 332 is oriented towards the user side such that emitted light propagates through the transparent and protective layer and to the eye. In another example, the radioluminescent light emitting device 332 is disposed on the user side of the body 310 (e.g., attached externally on the exterior surface of the body 310 on the user side). In this example, the radioluminescent light emitting device 332 is also oriented such that the emitted light propagates and to the eye.

Multiple types of the light emitting devices 332 are possible, including a gaseous tritium light source (GTLS), a promethium-based light source, a radium-based light source, among other radioisotope-based light sources. Radioluminescence occurs when ionizing radiation is emitted during radioactive decay and collides with an atom or molecule, exciting an electron to a higher energy state, which subsequently returns to its ground state releasing a photon in the process. A radioluminescent light source can be created by combining a radioisotope and a phosphor material. For instance, GTLS are fabricated by encapsulating tritium gas in a hermetically sealed phosphor coated glass capillary or tube. The light emitting device 332 can be produced by encapsulating, fully or partially, radioluminescent resources in a set of transparent housings, such as polymer, glass, metal, or fabric housings. For instance, GTLS can be made in small glass housings added to the light emitting device 332 as an array of light sources. To minimize the visual side-effects of the continuous phototherapy, a wavelength is selected based on phosphor material coating inside the GTLS. The wavelength is close to the maximum absorbance of rod cells (500 nm), but sufficiently far from the maximal absorbance of the blue (425 nm) or green cones (535 nm). The light intensity is also sufficiently high to induce rod hyperpolarization but low enough to prevent cone stimulation, which starts around $10^{12}$ photons/s/cm$^2$ on the retina. An irradiance on the retina of around $10^9$ to $10^{11}$ photons/s/cm$^2$ is suitable and achievable by radioluminescent light sources. The irradiance as a function of position on retina can also be tuned and this is useful since rods are more abundant peripheral to the macula, where cones dominate. This spatially variable irradiance can be achieved through light source shape, position, filtering, or reflector design, or lensing within the light emitting device 332. In particular, the radioluminescent light emitting device 332 includes optical waveguides, reflectors, filters and the like (and which are not controller electrically or electro-mechanically) to direct the emitted light towards the retina.

In the second example, the wearable phototherapy eye device 300 further includes the circuitry 340, the set of electrodes 334 (optional), and the set of shutters 350. The set of electrodes 334 (and any light sensors) can be part of or separate from the light source 330 that includes the radioluminescent light emitting device 332. The circuitry 340 is electrically coupled with the set of electrodes 334, but not with the radioluminescent light emitting device 332 (unlike FIG. 2). This coupling may allow for ERG, EOG, and/or eye lid light transmissivity measurements usable to maintain a transfer function and to control the emission of the light.

The set of shutters 350 allows the control of the light emission. Generally, the radioluminescent light emitting device 332 emits radioluminescent light towards or from the user eye side of the body 310. A shutter includes a low light transmissivity portion and, optionally, a high light transmissivity portion. The low light transmissivity portion has a transmissivity relative to the radioluminescent light below a transmissivity level (e.g., less than one percent light transmissivity) and can be referred to as an opaque portion. The high light transmissivity portion has a transmissivity relative to the radioluminescent light over a higher transmissivity level (e.g., more than ninety percent light transmissivity) and can be referred to as a transparent portion. The shutter varies an emission property of the radioluminescent light emitted from the radioluminescent light emitting device 332 based on a relative position between the low light transmissivity portion (e.g., the opaque portion) and the radioluminescent light radioluminescent light emitting device 332.

Different types of shutters are possible including mechanical shutters, electro-mechanical shutters, chemical-based shutters, and/or thermal-based shutters. Example shutters are further described in connection with FIGS. 4 and 5. If an electrical signal to the shutter is needed to control this shutter, the circuitry 340 can electrically be coupled with the shutter to provide the electrical signal.

The circuitry 340 can be similar to the circuitry 240 of FIG. 2 and includes, for example, a power source 341, a controller 342, a transceiver 343, and a set of sensors 344. The power source 341, the controller 342, the transceiver 343, and the set of sensors 344 can be similar to or the same as the power source 241, the controller 242, the transceiver 243, and the set of sensors 244 of FIG. 2, respectively. In the interest of avoiding redundant description, the power source 341, the controller 342, the transceiver 343, and the set of sensors 344 and their operations are not further described herein and the description of the controller 242, the transceiver 243, and the set of sensors 244 equally applies to the corresponding components of FIG. 3. In addition, the circuitry 340 can include other components to drive the shuttering depending on the type of the set of shutters 350. For example, for a shutter controllable via an electromagnetic field, the circuitry 340 can include a set of coils to generate the relevant electromagnetic field. Similarly, for a shutter controllable via a temperature change, the circuitry 340 can include a heat source (e.g., a set of electrical resistors) to vary the temperature as needed.

Figure 4:
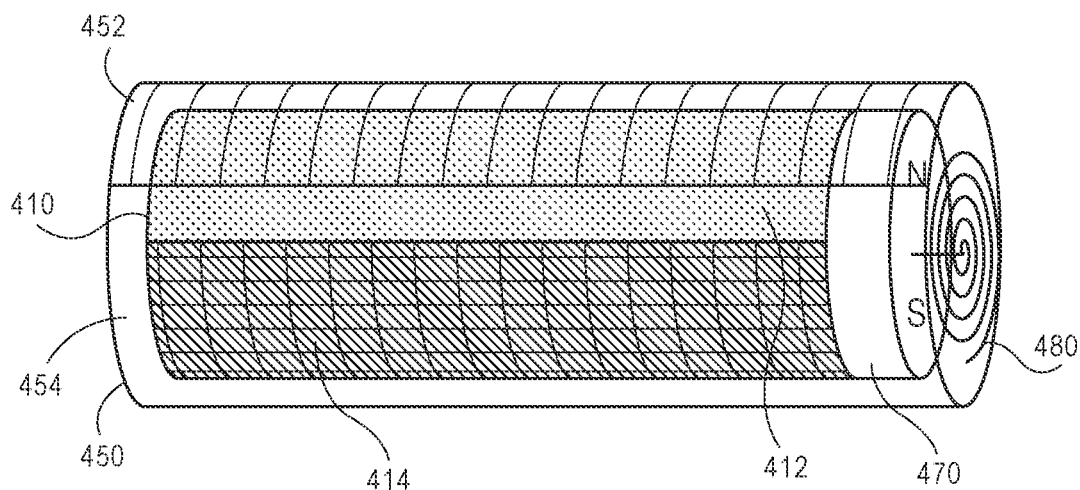
FIG. 4 illustrates an example of a shutter operable to control a light emission from a wearable phototherapy eye device, according to embodiments of the present disclosure.

FIG. 4 illustrates an example of a shutter 450 operable to control a light emission from a wearable phototherapy eye device, according to embodiments of the present disclosure. The control may depend on a rotational and concentric motion, whereby a relative position between an opaque portion 452 (e.g., corresponding to a low light transmissivity portion) of the shutter 450 and a light radioluminescent light source 410 is changed.

As illustrated, the shutter 450 includes a tubular housing. This housing includes the opaque portion 452 and a transparent portion 454 (e.g., corresponding to a high light transmissivity portion). In comparison, the light radioluminescent light source 410 includes a cylindrical housing that is disposed inside the tubular housing. The cylindrical housing also includes a transparent portion 412 and an opaque portion 414 (e.g., one coated with a right reflective material to direct the radioluminescent light for emission from the transparent portion 412). An emission property of the radioluminescent light source 410 (e.g., the irradiance) is varied based on a rotational movement of at least one of the cylindrical housing or the tubular housing such that the relative position between the transparent portion 412 of the light radioluminescent light source 410 and the opaque portion 452 of the shutter 450 is changed. In particular, the change to the amount of overlap between the opaque portion 452 and the transparent portion 412 corresponds to a change in the irradiance (e.g., the larger the overlap is, the smaller the irradiance becomes). When the opaque portion 452 fully covers the transparent portion 412, the amount of emitted light is significantly reduced to almost none.

In an example, the rotational movement is facilitated by a magnet 470 attached to an end of the radioluminescent light source 410. By altering the surrounding magnetic field, the radioluminescent light source 410 rotates within the shutter 450 along their parallel axis. The shuttering mechanism can be an active-off mechanism, where the change to the magnetic field would cause a rotation such that the opaque portion 452 fully covers the transparent portion 412. In this mechanism, a spring 480 is attached to the magnet 470 and the tubular housing of the shutter 450. The rotation loads the spring 480. Upon removal of the magnetic field, the loaded spring causes the radioluminescent light source 410 to rotate in the opposite direction. When the spring is unloaded (e.g., in a rested state), the overlap between the opaque portion 452 and the transparent portion 412 is significantly small or non-existent.

An active-on shuttering mechanism is also possible, where in the rested state of the spring 480, the opaque portion 452 fully covers the transparent portion 412 and, where in the loaded state of the spring 480, the overlap is significantly small or non-existent. Furthermore, although the radioluminescent light source 410 is rotated relative to the shutter 450, the shutter 450 can instead be rotated relative to the radioluminescent light source 410 (or both could be rotated at the same time) by attaching the magnet 470 to the tubular housing and the spring 480 to the cylindrical housing.

As an example of the active-off shuttering mechanism using a rotational motion, a cylindrical light source (e.g., the radioluminescent light source 410) can be produced with a hemi-circular reflector (e.g., corresponding to the opaque portion 414) such that light is principally emitted from the portion of the source without the reflector (e.g., the transparent portion 412). The light source is placed in a slightly larger tubular enclosure of a shutter (e.g., the shutter 450) such that the cylindrical light source is free to rotate along its axis. A portion of the enclosure is made transparent where it is desired that light be emitted from (e.g., the transparent portion 454). The remainder of the enclosure can be made opaque and non-reflective (e.g., the opaque portion 452). A magnet (e.g., the magnet 470) can be affixed to the end cylindrical light source in such a manner that it does not interfere with the ability of the light source to rotate along its axis. Furthermore, the magnet should be affixed in an orientation such that when an external magnetic field is applied, it rotates the light emitting face of the cylindrical light source away from the transparent portion of the enclosure. A means of returning the light source to its resting state orientation once the external magnetic field is removed can involve the use of another magnet affixed to the device, ferromagnetic material affixed to the device, a spring mechanism (e.g., the spring 480) affixed to the light source or magnet, hydrophilic/hydrophobic interactions such as between the surface of a portion of the light source and a portion of the enclosure possibly through a liquid, or other means that makes the resting state orientation one in which a low energy state for the system is achieved.

Figure 5:
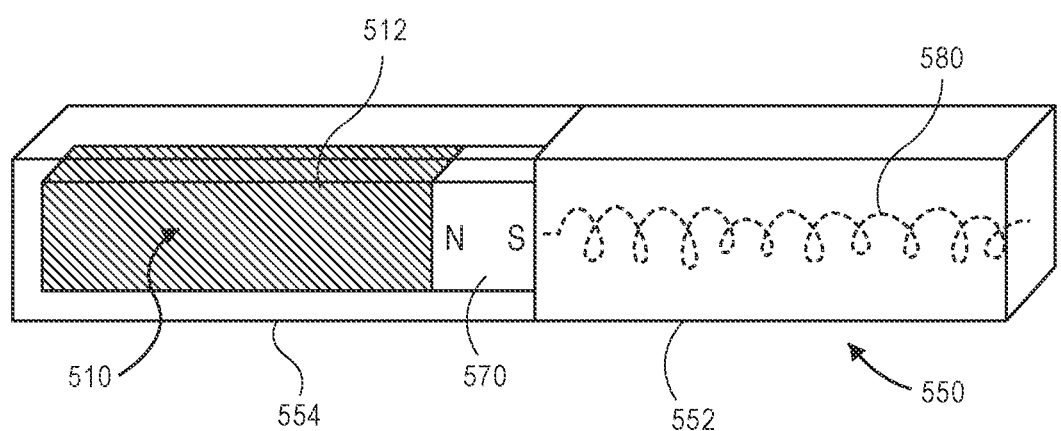
FIG. 5 illustrates another example of a shutter operable to control a light emission from a wearable phototherapy eye device, according to embodiments of the present disclosure.

FIG. 5 illustrates another example of a shutter operable to control a light emission from a wearable phototherapy eye device, according to embodiments of the present disclosure. The control may depend on a translational motion (e.g., linear actuation), whereby a relative position between an opaque portion 552 (e.g., corresponding to a low light transmissivity portion) of the shutter 550 and a light radioluminescent light source 510 is changed.

As illustrated, the shutter 550 includes an enclosure. This enclosure includes the opaque portion 552 and a transparent portion 554 (e.g., corresponding to a high light transmissivity portion). In comparison, the light radioluminescent light source 510 includes a prismatic housing. This housing also includes a transparent portion 512 and, optionally, an opaque portion (e.g., one coated with a right reflective material to direct the radioluminescent light for emission from the transparent portion 512). An emission property of the radioluminescent light source 510 (e.g., the irradiance) is varied based on a translational movement of at least one of the prismatic housing relative to the enclosure or the enclosure relative to the prismatic housing such that the relative position between the transparent portion 512 of the light radioluminescent light source 510 and the opaque portion 552 of the shutter 550 is changed. In particular, the change to the amount of overlap between the opaque portion 552 and the transparent portion 512 corresponds to a change in the irradiance (e.g., the larger the overlap is, the smaller the irradiance becomes). When the opaque portion 552 fully covers the transparent portion 512, the amount of emitted light is significantly reduced to almost none.

In an example, the translational movement is facilitated by a magnet 570 attached to an end of the radioluminescent light source 510. By altering the surrounding magnetic field, the radioluminescent light source can be actuated in or out of the enclosure the shutter 550 along their parallel axis. The shuttering mechanism can be an active-off mechanism, where the change to the magnetic field would cause an insertion of the radioluminescent light source 510 into the enclosure of the shutter 550 such that the opaque portion 552 fully covers the transparent portion 512. In this mechanism, a spring 580 is attached to the magnet 570 and the enclosure of the shutter 550. The actuation loads the spring 580. Upon removal of the magnetic field, the loaded spring causes the radioluminescent light source 510 to actuate out from the enclosure of the shutter 550. When the spring is unloaded (e.g., in a rested state), the overlap between the opaque portion 552 and the transparent portion 512 is significantly small or non-existent.

An active-on shuttering mechanism is also possible, where in the rested state of the spring 580, the opaque portion 552 fully covers the transparent portion 512 and, where in the loaded state of the spring 580, the overlap is significantly small or non-existent. Furthermore, although the radioluminescent light source 510 is actuated relative to the shutter 550, the shutter 550 can instead be actuated relative to the radioluminescent light source 510 (or both could be rotated at the same time) by attaching the magnet 570 to the tubular housing and the spring 580 to the cylindrical housing.

As an example of the active-off shuttering mechanism using a translational motion, a light source with a prismatic shape (e.g., radioluminescent light source 510) can be placed into an enclosure (e.g., the enclosure of the shutter 550), with a profile and length that allows the light source to slide inside it. If a portion of the enclosure is transparent to the emitted light from the source (e.g., the transparent portion 554), while other portions are not transparent (e.g., the opaque portion 552), then the movement of the light source within the enclosure can change the degree of light emission from the device. By affixing a magnet (e.g., the magnet 570) to the light source, an external magnetic field can drive actuation of the light source within the enclosure. In this manner, the light source can be moved from a transparent portion of the enclosure to a non-transparent portion of the enclosure, resulting in attenuated light emission from the device. A means of returning the light source to its resting state orientation once the external magnetic field is removed can involve the use of another magnet affixed to the light source, ferromagnetic material affixed to the enclosure, a spring mechanism (e.g., the spring 580) affixed to the light source or magnet, hydrophilic/hydrophobic interactions such as between the surface of a portion of the light source and a portion of the enclosure possibly through a liquid, or other means that make the resting state orientation one in which a low energy state for the system is achieved.

The rotational motion as illustrated in FIG. 4 and the translational motion as illustrated in FIG. 5 can be used in combination. In particular, a radioluminescent light source can have a cylindrical housing and a shutter can have a tubular enclosure. This light source can be actuated in and out of the shutter, while also being rotated along their parallel axis.

Other shuttering mechanisms are also possible. In an example of a shuttering mechanism, a light source includes a housing that has a first pattern of transparent gratings and opaque gratings. A shutter includes an enclosure that has a second pattern of transparent gratings and opaque gratings. The emission property of light from the light source is varied based on at least one of a translational movement or a rotational movement of at least one of the housing or the enclosure such that the relative position between the first pattern and the second pattern is changed.

In particular, the degree of motion required to transition between a high illumination state to a low illumination state can be significantly reduced through the use of complementary gratings. For example, if the light source is patterned with transparent and non-transparent gratings and the shuttering mechanism, sheath, or enclosure is patterned with similar gratings than the relative movement of only a grating width is sufficient to transition from a high illumination state to a low illumination state. This type of patterning can be used with shuttering mechanisms relying on both rotational and axial motions.

In an another example of shuttering mechanisms, an active-off shuttering mechanism involves affixing a magnetic element to a shutter, which is secured in such a manner that it maintains certain degrees of freedom, but has a resting state that allows illumination from a light source in a given direction. Upon activation of the shuttering mechanism, such as with the use of an external magnetic, the shutter re-orients itself so that illumination is directed in a different direction.

In an another example of shuttering mechanisms, a light source includes a cylindrical housing that has a transparent portion. A shutter includes a hemi-circular housing that has an opaque portion. The emission property is varied based on a rotational movement of the hemi-circular housing relative to the cylindrical housing such that the relative position between the transparent portion and the opaque portion is changed.

In particular, the shutter can be produced with a hemi-circular shape such that when positioned around the cylindrical light source it causes light to be emitted in a directional manner. The shutter is made slightly larger than the cylindrical light source such that it is free to rotate around it but otherwise affixed, such as by means of bands, endcaps, or an enclosure structure, so that it maintains its coaxial mate with the cylindrical light source. The shutter may itself be composed of a tubular structure in which a portion of the tube is transparent and a portion is non-transparent (e.g. opaque or reflective). A magnet can be affixed to the shutter in such a manner that it does not interfere with the ability of the shutter to rotate around the light source. Furthermore, the magnetic can be affixed in an orientation such that when an external magnetic field is applied, it rotates the shutter to reduce illumination in the desired direction. A means of returning the shutter to its resting state orientation once the external magnetic field is removed can involve the use of another magnet affixed to the device, ferromagnetic material affixed to the device, a spring mechanism affixed to the shutter or magnet, hydrophilic/hydrophobic interactions possibly through a liquid, or other means that make the resting state orientation one in which a low energy state for the system is achieved.

Similarly, a shutter can be made that is able to slide over a light source with a prismatic shape. By affixing a magnet to the shutter, an external magnetic field can drive actuation of the shutter to cover more or less of the light source. A means of returning the shutter to its resting state orientation once the external magnetic field is removed can involve the use of another magnet, ferromagnetic material, a spring mechanism, hydrophilic/hydrophobic interactions, or other means that make the resting state orientation one in which a low energy state for the system is achieved.

In an another example of shuttering mechanisms, a shutter includes a reservoir and a transparent channel that is positioned between a light source and the user side. The reservoir includes a ferrofluid, wherein the emission property is varied based on an amount of the ferrofluid in the transparent channel from the reservoir. Hence, by moving the amount of ferrofluid into the transparent channel, a portion of this channel that receives the ferrofluid becomes opaque. This portion corresponds to the low light transmissivity portion of the shutter.

In particular, a ferrofluid is encapsulated around the light source and can be moved using an external magnetic field to obstruct light emission from a desired portion of the light source. A means of returning the ferrofluid to its resting position once the external magnetic field is removed can involve the use of another magnet affixed to the device, ferromagnetic material affixed to the device, or hydrophilic/hydrophobic interactions. For example, a reservoir may hold the majority of the ferrofluid in the resting state, but an external magnetic field can be used to pull the ferrofuid into a channel overtop of the illuminating surface to attenuate light emission.

In an another example of shuttering mechanisms, an active-off shuttering mechanism involves the use of shutter constructed of magneto-optical material that possesses light transmissibility in the resting state, but whose transmissibility can be changed by subjecting it to an external magnetic field.

In an another example of shuttering mechanisms, a shutter includes an optical waveguide that has an opaque gate. The emission property of light emitted from a light source is varied based on a movement of the opaque gate. The opaque gate corresponds to the low light transmissivity portion of the shutter.

In particular, a gated or light-valved optical fiber is used and through which light from the light source travels to be delivered to a desired target. When the gate is open, light can pass through and shine onto the desired target. However, when the gate is closed the light intensity on the target is attenuated. Various means of gating the optical fiber are possible, some of which may rely on onboard electrical power to activate, including Faraday rotator, physical gate in the light path (e.g., ferrofluid, magnetic actuator), liquid crystal light valve, electrochromics, photochromic, thermochromic, suspended particles, and micro-blinds. These gating means may also be employed to act as a shutter directly around the light source.

Figure 6:
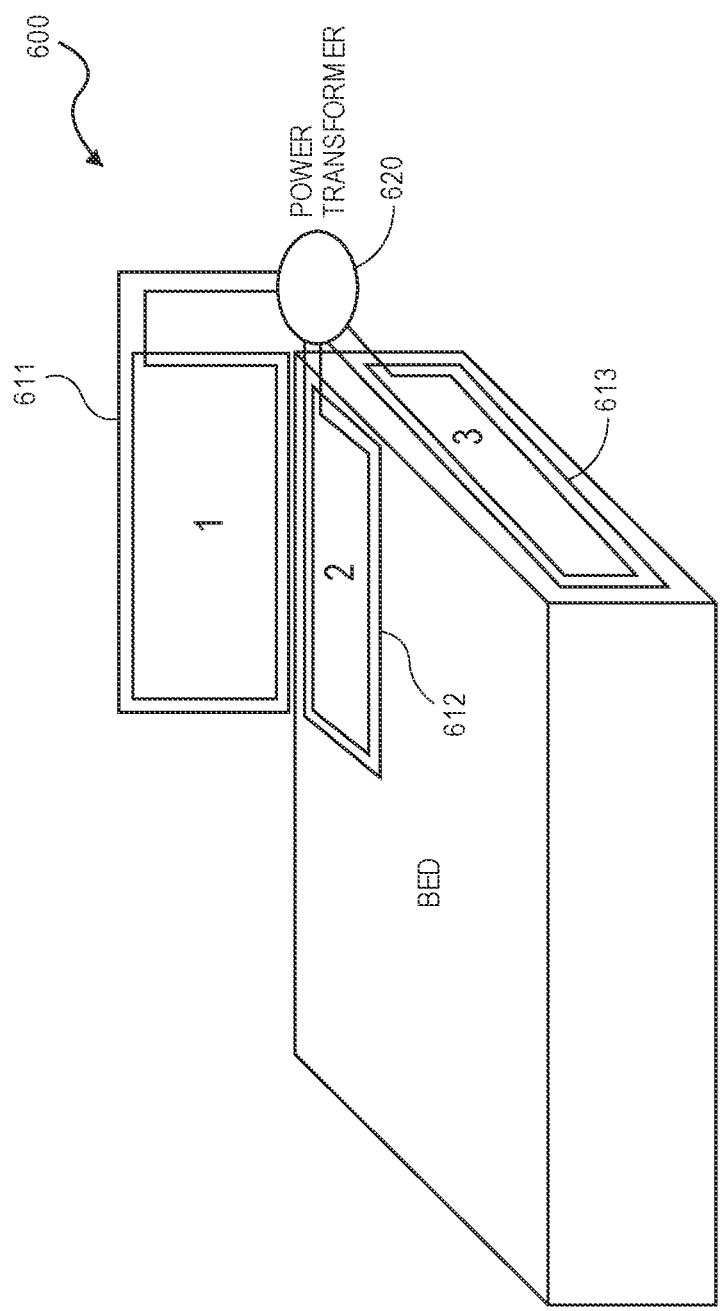
FIG. 6 illustrates an example of an external power supply system operable to wirelessly transmit power to a wearable phototherapy eye device, according to embodiments of the present disclosure.

FIG. 6 illustrates an example of an external power supply system 600 operable to wirelessly transmit power to a wearable phototherapy eye device, such as any of the wearable phototherapy eye devices of FIGS. 1-3 and FIGS. 7-9, according to embodiments of the present disclosure. As illustrated, the power supply system 600 includes a set of transmission coils and a power transmitter 620. The set may include multiple transmitting coils at orthogonal orientations to ensure efficient wireless power transfer regardless of how the user orients their head and, equivalently, the wearable phototherapy eye device. As illustrated, this set includes a first transmission coil 611 in the Z-plane, a second transmission coil 612 in the X-plane, and a third wireless transmission coil 613 in the Y-plane. These coils can be placed around the sleeping area of the user in the orthogonal orientations to ensure good coupling to the receiving coils of the wearable phototherapy eye device. For instance, the transmission coils may be placed under the sheet, mattress or pillow (e.g., the second transmission coil 612), along the mattress (e.g., the third transmission coil 613), and/or along the head board (e.g., the first transmission coil 611). The power transmitter 620 may select one or more of the transmission coils for wireless power transmission and may supply the electrical current to the selected transmission coil(s). Orientation data of the wearable phototherapy eye device can be transmitted to the power supply system 600 to trigger a selection of a particular transmission coil(s) by the power transmitter 620.

Figure 7:
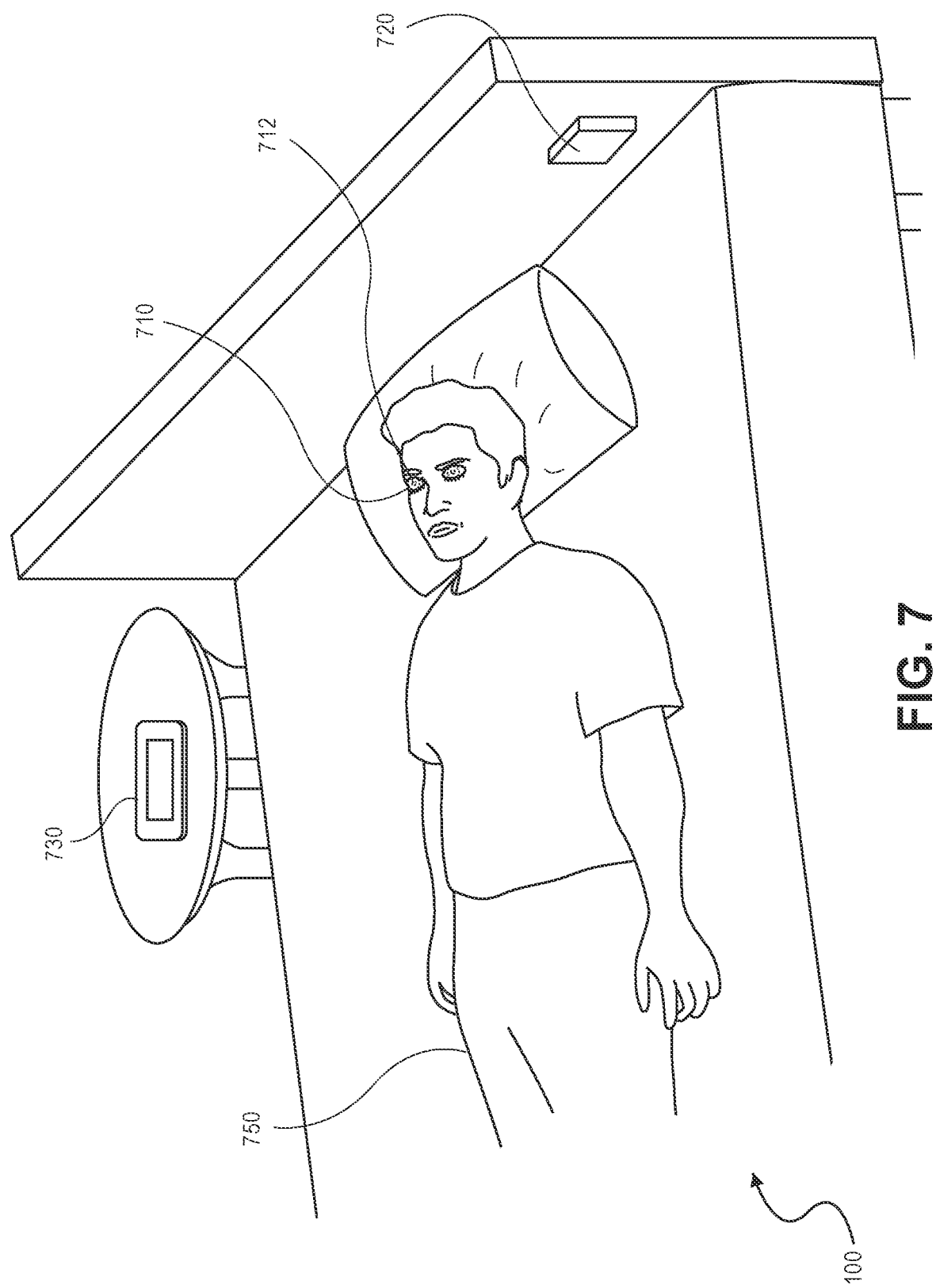
FIG. 7 illustrates another example of a wearable phototherapy eye system, according to embodiments of the present disclosure.

FIG. 7 illustrates another example of a wearable phototherapy eye system 700, according to embodiments of the present disclosure. As illustrated, the phototherapy eye system 700 includes a phototherapy lens 710, a power source 720, and a computing device 730. The phototherapy lens 710 is an example of a wearable phototherapy eye device, similar to the wearable phototherapy eye device 110 of FIG. 1 except that the components thereof are packaged in a lens that can be placed on a user's 150 cornea (e.g., as a phototherapeutic contact lens, further described in connection with FIG. 8) or implanted in the user's 150 eyeball (as a phototherapeutic intraocular lens, further described in connection with FIG. 9). The user 750 may wear the phototherapy lens 710 (as a contact lens or as an implanted intraocular lens following an implantation procedure by a physician) for phototherapy treatment. The power source 720 may supply electrical power to the phototherapy lens 710. The computing device 730 may provide instructions and/or data controlling certain operations of the phototherapy eye device 710. Although FIG. 7 illustrates these components being separate from each other, some or all of the components can be integrated. For instance, the phototherapy lens 710 can include the power source 720 and/or the computing device 730.

Generally, the components of the phototherapy lens 710 are similar to those of the wearable phototherapy eye device 110 of FIG. 1 and shown in FIGS. 2-5. In addition, the power source 720 and the computing device 730 are similar to the power source 120 and the computing device 130 of FIG. 1, respectively. In the interest of avoiding redundant description, similarities between the components are not repeated herein. Nonetheless, the above descriptions of the components applies herein to the phototherapy lens 710, the power source 720, and the computing device 730.

In an example, the phototherapy lens 710 includes at least one light source 712 per eye of the user 750. Upon wearing the phototherapy lens 710, each light source 712 is positioned to be on or in the corresponding eye such that light emitted from the light source 712 propagates towards the retina of the eye. In particular, the light source 712 may be substantially centered relative to the pupil of the eye. The power source 720 can supply power to the phototherapy lens 710 using different means for power transmission, including wireless power transmission. The computing device 730 generally includes a memory storing computer-readable instructions and a processor suitable for execution of the instructions such that, upon execution, the computing device 730 can perform various programmed operations related to phototherapy.

Figure 8:
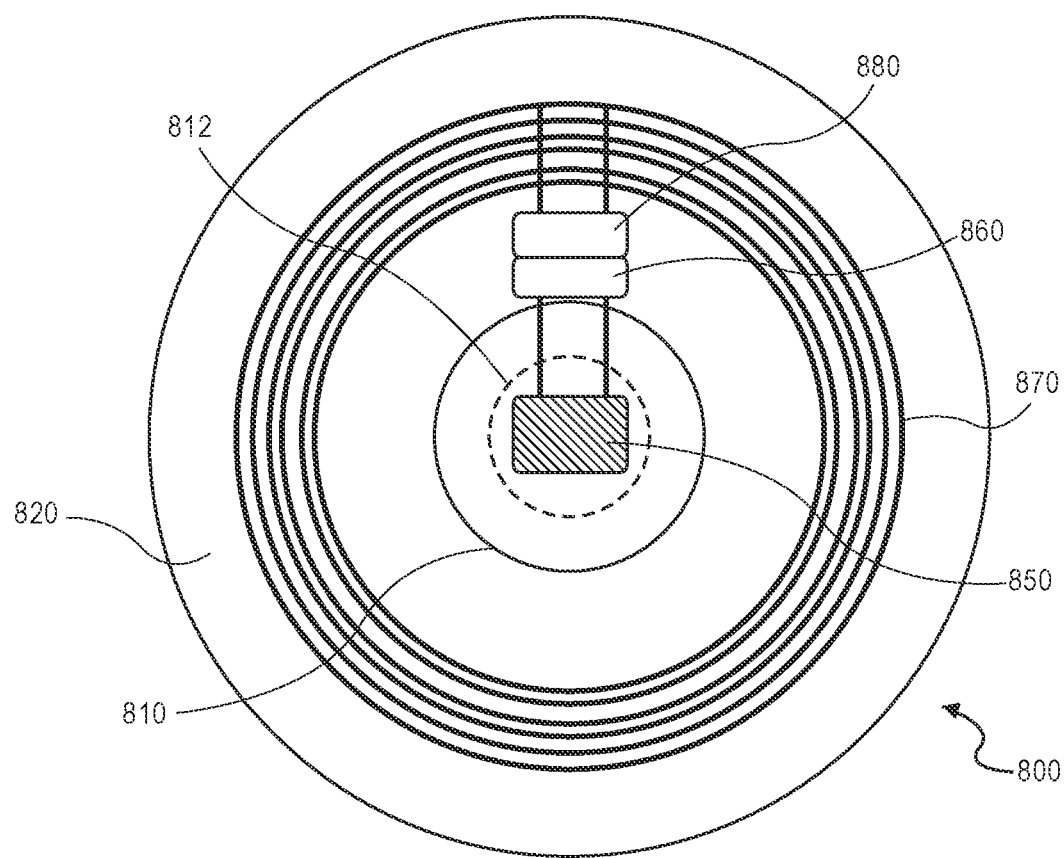
FIG. 8 illustrates an example of a phototherapy lens operable as a wearable phototherapy eye device, according to embodiments of the present disclosure.

FIG. 8 illustrates an example of a phototherapy lens operable as a wearable phototherapy eye device, according to embodiments of the present disclosure. As illustrated, the phototherapy lens is a phototherapeutic contact lens 800. The phototherapeutic contact lens 800 includes a lens body that, in turn, includes a transparent optical zone 810 that has a user side. The lens body also includes a periphery 820 outside of the transparent optical zone 810. A light source 850 is disposed within the transparent optical zone 810 and is configured to emit light towards the user eye side. A controller 860 is disposed within the transparent optical zone 810 or the periphery 820, is electrically coupled with the light source 850, and is configured to vary an emission property of the light. The phototherapeutic contact lens 800 also includes a receiving coil 870 disposed within the periphery 820 and configured to induce electrical current based on a wireless power transmission from a transmission coil. Further, the phototherapeutic contact lens 800 includes a converter disposed within the transparent optical zone 810 or the periphery 820 and configured to convert the induced electrical current into a converted electrical current. Power to the controller is available based on the converted electrical current.

The converter, the controller 860, and/or the receiving coil 870 can be a component within circuitry 880. This circuitry 880 can be disposed entirely within the transparent optical zone 810 (excluding, for instance, the receiving coil 870), the periphery 820, or distributed between the optical zone 810 and the periphery 820. The circuitry 880 can additionally include a transceiver, a set of sensors, and a set of electrodes, similar to the transceiver 243, the set of sensors 244, and the set of electrodes 234, respectively, of FIG. 2. In particular, the transceiver is configured to transmit and receive data and computer-readable instructions. The set of sensors is configured to measure phototherapy-related data, such as a wear time of the phototherapeutic lens 800, a motion of the phototherapeutic lens 800 (device motion), and user motion. The set of electrodes can be configured to measure ERG and/or EOG responses that are then usable to generate and/or maintain a transfer function of the light from the phototherapeutic lens 800 to the retina. In addition, the controller 860 can be similar to the controller 242 of FIG. 2, the converter can be similar to the converter of the power source 241 of FIG. 2, and the receiving coil 870 can be similar to one or more of the receiving coils of the power source 241 of FIG. 2. In the interest of avoiding redundant description, the converter, the controller 860, the receiving coil 870, and the circuitry 880 and their operations are not further described herein and the description of the converter of the power source 241, the controller 242, the receiving coil(s) of the power source 241 and remaining components of the circuitry 240 of FIG. 2 equally applies to the corresponding components of FIG. 8.

In an example, the transparent optical zone 810 is transparent (e.g., having a light transmissivity level over a transmissivity threshold) to at least the light emitted from the light source and to light in the physical environment. Further, the transparent optical zone 810 has a circular shape defined by a radius. The radius is at least equal to or larger than the average radius of a dilated pupil of a human eye (e.g., 3.5 mm), such that when the eye lid is open in dark conditions and the pupil is dilated, the transparent optical zone 810 does not block the light from the physical environment. The radius can extend to be close to the edge of the lens body, while leaving sufficient room for coil and other circuitry placement in the periphery 820. For instance, the periphery 820 can be made to have a width less than 5 mm.

Generally, when worn by the user, the transparent optical zone 810 is centered over the pupil and extends to at least the edge of the dilated pupil. The periphery 820 can extend from that point on to the outer edge of the lens body. Typically, the periphery 820 is positioned over the iris. The periphery 820 may, but need not, be made of the same transparent material as the one in the transparent optical zone 810. In other words, the periphery 820 can also be transparent.

Within the transparent optical zone 810, an inner circle can be defined as having a radius less than the average radius of a constricted pupil of the human eye (e.g., 2 mm). The inner circle and the circular shape of the transparent optical zone 810 may be concentric. The light source 850 is typically positioned within the inner circle. In a specific example, the light source 850 is positioned about the center of the circular shape, and the controller 860 and the converter are disposed within the periphery.

The light source 850 includes a set of electroluminescent light sources such as a set of light emitting diodes or organic light emitting diodes. An electroluminescent light source of the light source 850 can have an emitting side and an opaque side. Light is emitted out from the emitting side, and this emitting side is oriented towards the user side such that the light travel towards the retina. The opaque side can be opposite to the emitting side and is opaque to (or reflective of) the light such that the light is not emitted away from the user side.

In an example, the phototherapeutic contact lens 800 can be produced by combining a light source (e.g., electroluminescent emitters, organic light emitting devices, light emitting devices, light emitting cells, light emitting electrochemical cells) and power source (e.g. inductive coupling, resonant inductive coupling, capacitive coupling, magnetodynamic coupling, light waves) and embedding them into a contact lens with optional control circuitry. Means of embedding components into lenses are further described in connection with FIGS. 10 and 11. In one illustration, an electroluminescent light source (e.g., the light source 850) is used. It is powered from wireless power transfer using inductive coupling between a powering coil and a receiving coil (e.g., the receiving coil 870). The receiving coil is connected to a circuit to convert the induced current to an appropriate signal to drive the light emitting diode. For instance, the receiving coil may connect to an AC-DC converter, which may connect to a DC-DC converter, which may connect to control circuitry (e.g., the controller 860 and the circuitry 880) which may drive the light emitting diode. This circuitry may allow for wireless communication to and from the contact lens. This wireless communication may be used to adjust the light emission properties of the lens, to relay positioning information of the lens, to relay information on the duration of use, ERG measurements, EOG measurements, etc.

Control logic, stored as computer-readable instructions on the controller 860 or on a remote computing device or implemented via specialized hardware on the controller or on the remote computing device, can be used to optimally control the intensity of the light emission from the contact lens over the duration of wear (including, dependently on a sleep phase, an emission target of the sleep phase, and a transfer function of the light to the retina). For instance, by using the motion of the lens, the motion of the user, the time of night, or other means, the sleep phase of the user can be monitored. This information can then be used to control the intensity of light emission from the contact lens. For example, it may be beneficial to turn light emission on once the patient has fallen asleep so as not to provide a distraction while the user is conscious. In another example, the light intensity may be ramped up or down according to the sleep phase of the user. In another example, the light intensity of the lens may be titrated over a period of time (e.g., days to weeks) as the user acclimatizes to sleep with illumination. In this way, a more effective dose can be given while mitigating the risk that the user will experience sleep disturbance or gets annoyed with the therapy and stop using it all together.

Figure 9:
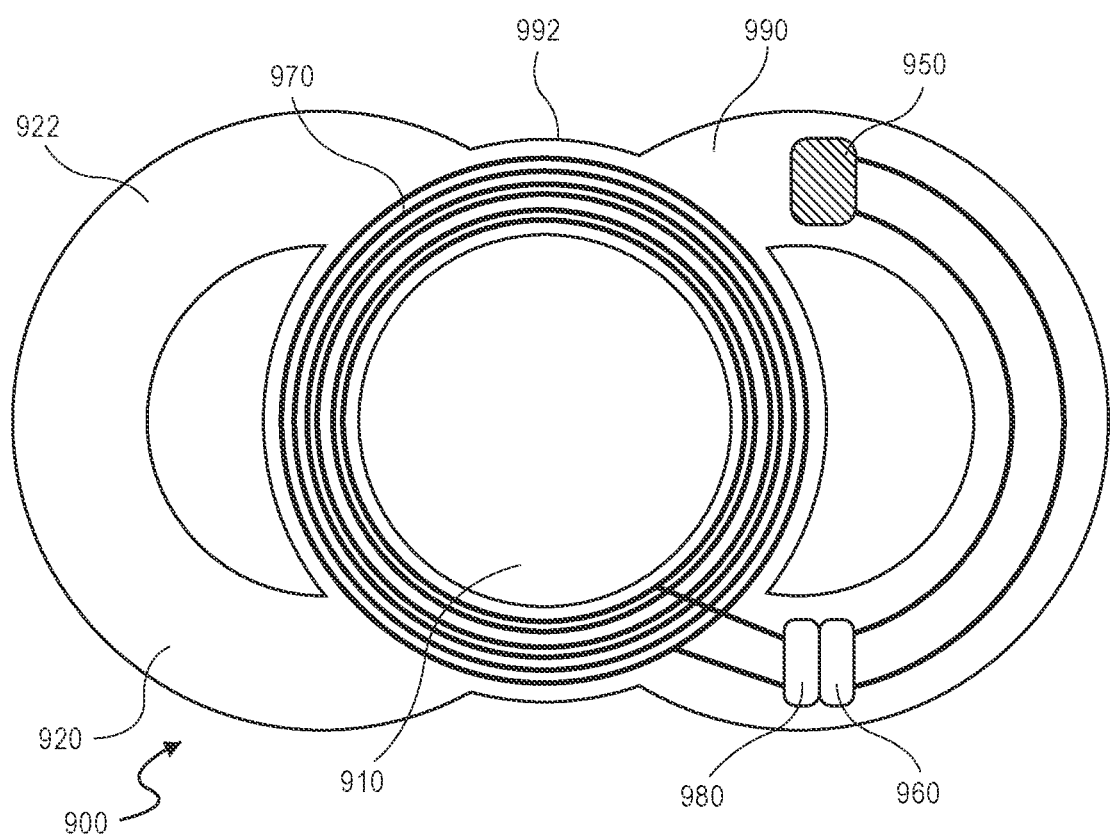
FIG. 9 illustrates another example of a phototherapy lens operable as a wearable phototherapy eye device, according to embodiments of the present disclosure.

FIG. 9 illustrates another example of a phototherapy lens operable as a wearable phototherapy eye device, according to embodiments of the present disclosure. As illustrated, the phototherapy lens is a phototherapeutic intraocular lens 900. The phototherapeutic intraocular lens 900 includes a lens body that, in turn, includes a transparent optical zone 910 that has a user side. The lens body also includes a periphery 920 outside of the transparent optical zone 910. The periphery 920 can include haptics 922 to secure the intraocular lens 900 in place once implanted inside the eyeball. A light source 950 is disposed within the transparent optical zone 910 or the periphery 920 and is configured to emit light towards the user eye side. Unlike the contact lens 800 of FIG. 8, the periphery 920 is a possible location for the light source 950 because this lens 900 would be implanted inside the eyeball and the light emitted by the light source would not be reflected back by the iris (whereas, that may be the case with the contact lens 800 if the periphery is used to house the light source 850).

A controller 960 is disposed within the transparent optical zone 910 or the periphery 920, is electrically coupled with the light source 950, and is configured to vary an emission property of the light. The phototherapeutic intraocular lens 900 also includes a receiving coil 970 disposed within the periphery 920 and configured to induce electrical current based on a wireless power transmission from a transmission coil. Further, the phototherapeutic intraocular lens 900 includes a converter disposed within the transparent optical zone 910 or the periphery 920 and configured to convert the induced electrical current into a converted electrical current. Power to the controller is available based on the converted electrical current.

The converter, the controller 960, and/or the receiving coil 970 can be a component within circuitry 980. This circuitry 980 can be disposed entirely within the transparent optical zone 910 (excluding, for instance, the receiving coil 970), the periphery 920, or distributed between the optical zone 910 and the periphery 920. The circuitry 980 can additionally include a transceiver, a set of sensors, and a set of electrodes, similar to the transceiver 243, the set of sensors 244, and the set of electrodes 234, respectively, of FIG. 2. In particular, the transceiver is configured to transmit and receive data and computer-readable instructions. The set of sensors is configured to measure phototherapy-related data, such as a wear time of the phototherapeutic lens 900, a motion of the phototherapeutic lens 900 (device motion), and user motion. The set of electrodes can be configured to measure ERG and/or EOG responses that are then usable to generate and/or maintain a transfer function of the light from the phototherapeutic lens 900 to the retina. In addition, the controller 960 can be similar to the controller 242 of FIG. 2, the converter can be similar to the converter of the power source 241 of FIG. 2, and the receiving coil 970 can be similar to one or more of the receiving coils of the power source 241 of FIG. 2. In the interest of avoiding redundant description, the converter, the controller 960, the receiving coil 970, and the circuitry 980 and their operations are not further described herein and the description of the converter of the power source 241, the controller 242, the receiving coil(s) of the power source 241 and remaining components of the circuitry 240 of FIG. 2 equally applies to the corresponding components of FIG. 9.

In an example, the transparent optical zone 910 is transparent (e.g., having a light transmissivity level over a transmissivity threshold) to at least the light emitted from the light source and to light in the physical environment. The transparent optical zone 910 can have a similar design as the transparent optical zone 810 of FIG. 8. However, its dimensions and geometry can be different given that the intraocular lens 900 would be implanted in the eyeball.

The light source 950 includes a set of electroluminescent light sources such as a set of light emitting diodes or organic light emitting diodes. An electroluminescent light source of the light source 950 can have an emitting side and an opaque side. Light is emitted out from the emitting side, and this emitting side is oriented towards the retina. The opaque side can be opposite to the emitting side and is opaque to (or reflective of) the light such that the light is not emitted out of the eyeball. Different locations of the light source 950 are possible. For example, the light source can be centered in the optical transparent zone 910. Alternatively, the light source 950 can be positioned within the periphery 920. If the periphery 920 is transparent, the light can still be emitted towards the retina. If the periphery 920 is not transparent, this periphery 920 can include a set of light guides 990 (e.g., optical waveguides) and a light diffusor or emitter 992. The light emitted by the light source 950 travels within the set of light guides 990 and is emitted out from the light diffusor or emitter 992.

In an example, the phototherapeutic intraocular lens 900 can be produced by combining a light source (e.g., electroluminescent emitters, organic light emitting devices, light emitting devices, light emitting cells, light emitting electrochemical cells) and power source (e.g. inductive coupling, resonant inductive coupling, capacitive coupling, magnetodynamic coupling, light waves) and embedding them into an intraocular lens with optional control circuitry. Means of embedding components into lenses are further described in connection with FIGS. 10 and 11. In one illustration, an electroluminescent light source (e.g., the light source 950) is used. It is powered from wireless power transfer using inductive coupling between a powering coil and a receiving coil (e.g., the receiving coil 970). The receiving coil is connected to a circuit to convert the induced current to an appropriate signal to drive the light emitting diode. For instance, the receiving coil may connect to an AC-DC converter, which may connect to a DC-DC converter, which may connect to control circuitry (e.g., the controller 960 and the circuitry 980) which may drive the light emitting diode. This circuitry may allow for wireless communication to and from the intraocular lens. This wireless communication may be used to adjust the light emission properties of the lens, to relay positioning information of the lens, to relay information on the duration of use, ERG measurements, EOG measurements, etc.

Control logic, stored as computer-readable instructions on the controller 960 or on a remote computing device or implemented via specialized hardware on the controller or on the remote computing device, can be used to optimally control the intensity of the light emission from the intraocular lens over the duration of wear (including, dependently on a sleep phase, an emission target of the sleep phase, and a transfer function of the light to the retina). For instance, by using the motion of the lens, the motion of the user, the time of night, or other means, the sleep phase of the user can be monitored. This information can then be used to control the intensity of light emission from the intraocular lens. For example, it may be beneficial to turn light emission on once the patient has fallen asleep so as not to provide a distraction while the user is conscious. In another example, the light intensity may be ramped up or down according to the sleep phase of the user. In another example, the light intensity of the lens may be titrated over a period of time (e.g., days to weeks) as the user acclimatizes to sleep with illumination. In this way, a more effective dose can be given while mitigating the risk that the user will experience sleep disturbance or gets annoyed with the therapy and stops using it all together.

FIGS. 1-5 and 7-9 illustrate the use of a light source in a wearable phototherapeutic eye device. Additionally or alternatively, upconverting crystals can be used to convert a wavelength of emitted light to a target wavelength, where the target wavelength is used for the phototherapy. In this way, if there are multiple subjects in a physical environment, a light that may not be visible and/or disruptive to any of the subjects may be emitted within this environment. The subject of the phototherapy can rely on the upconverting crystals to convert the emitted light to the target wavelength, where these crystals can be included in the wearable phototherapeutic eye device and/or the eyeball(s) of the subject. Remaining subjects that are not targeted by the phototherapy may not use upconverting crystals. Hence, the upconverting crystals can be integrated with any of the wearable phototherapeutic eye devices of FIGS. 1-5 and 7-9 or can be implanted directly in the eyeball(s). The integration can include adding these crystals as a film or a layer disposed between a wearable phototherapeutic eye device and a user eye (or the user retina in case of an intraocular phototherapeutic lens).

In an example, upconverting crystals may provide a means of generating light to illuminate an eye. They can be incorporated into a contact lens, an intraocular lens, an ocular implant, or a sleep mask. By illuminating the upconverting crystals with an appropriate light source (e.g., adequate intensity and wavelength within the absorption/excitation band of the crystals), a longer wavelength light source can be converted into a shorter wavelength light source. This has several advantages. Firstly, there is a known infrared window to which tissue has relatively high transmissivity compared to the visible spectrum, allowing the light to more efficiently penetrate inside the body. Secondly, it is possible to use wavelengths sufficiently long that they are not detected by the visual system. Thus an area can be illuminated with longer wavelength light, unnoticed by those in the vicinity, and only converted to shorter wavelength light where the upconverting crystals are. Thirdly, longer wavelengths can be converted into wavelengths that have therapeutic value such as for phototherapy.

For instance, upconverting crystals can be incorporated into a contact lens, an intraocular lens, an ocular implant. The sleeping area of the patient is illuminated with an appropriate wavelength light able to reach and excite the upconverting crystals. The upconverting crystals emit light at a therapeutic wavelength to the eye. Those in the vicinity of the illumination without devices containing upconverting crystals are undisturbed if a wavelength outside the visual range is chosen.

Lenses, including contact lenses and intraocular lenses, provide a convenient means of anchoring the phototherapeutic device to the eye in a reversible manner and for encapsulating the components of the phototherapeutic system to protect them from damage from the users and to isolate the user from potentially harmful components. For long term wear (e.g. overnight use), it may be advantageous that the lens has sufficiently high oxygen permeability to allow the underlying cornea to receive adequate oxygen, which mitigates corneal swelling (or the retina to receive adequate oxygen in the case of intraocular lenses). It becomes increasingly difficult to overcome this permeability challenge when the lens is encapsulating components due to the increased thickness of the lens and often low oxygen permeability of encapsulated components. As disclosed herein, embodiments of the present disclosure resolve this challenge by providing a multi-layer lens, having one or more gaps sufficiently large to contain the phototherapy-related components and a highly permeable oxygen material to allow the proper flow of the oxygen through the lens.

Figure 10:
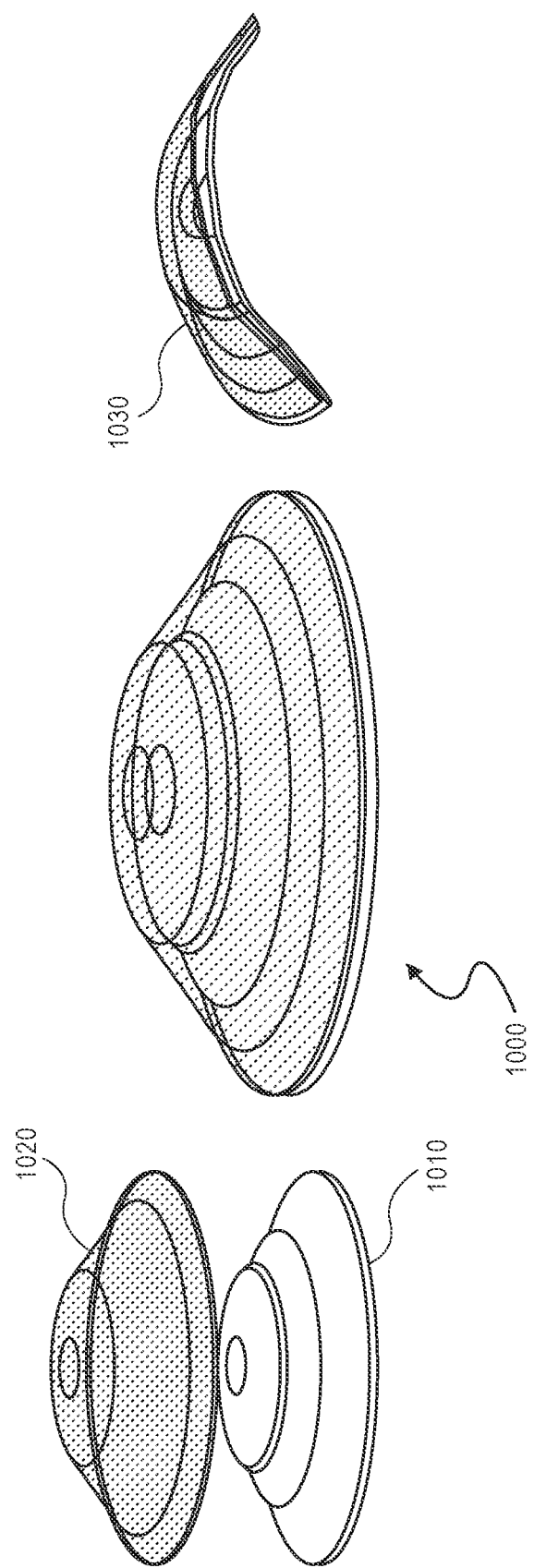
FIG. 10 illustrates an example of an assembly of a lens configurable as a phototherapy lens, according to embodiments of the present disclosure.

FIG. 10 illustrates an example of an assembly of a lens 1000 configurable as a phototherapy lens, according to embodiments of the present disclosure. The lens 1000 can be a phototherapeutic contact lens, such as the phototherapeutic contact lens 800 of FIG. 8, or a phototherapeutic intraocular lens, such as the phototherapeutic intraocular lens 900 of FIG. 9. Generally, the lens 1000 includes multiple lens layers and one or more gaps between the layers. Each layer may represent a lens on its own and can designed for specific optical properties. Each gap is designed as a space where phototherapy-related components of the lens 1000 (e.g., light source, power source, controller, transceiver, sensors, electrodes, etc.) can be contained, and where this space is highly permeable to oxygen such that the oxygen can flow properly through the lens 1000 to the user eye or retina.

As illustrated in FIG. 10, the lens 1000 includes two lens layers and a gap 1030 (although a larger number of layers and/or gaps is possible). A first lens layer 1010 is a first lens and would be in contact with the user eye. Accordingly, this layer 1010 may be referred to as a contact lens. A second layer 1020 is a second lens, would not be in contact with the user eye, and would be positioned away from the user eye based on the gap 1030. For instance, this second layer 1020 is a vision-correction lens. The phototherapy-related components can be disposed within the gap 1030. Air, or other highly permeable oxygen and transparent material can fill the remainder of the gap 1030. Various permeable oxygen and transparent materials are possible including, for instance, perfluorocarbon, silicone, Vycor 7930 (a VYCOR material available from Corning, Inc. of New York, U.S.A.) and other nano-porous glasses. In this way, when the lens 1000 is worn by the user, oxygen flows from the surrounding physical environment into the gap 1030 through the second layer 1020 and out from the gap 1030 into the user eye through the first layer 1010.

In addition, prior to forming the lens 1000, any or all of the phototherapy-related components (e.g., light source, power source, controller, transceiver, sensors, electrodes, etc.) can be coated with or dipped in a permeable oxygen and transparent material, then placed in the gap 1030 prior to mating the first and second layers 1010 and 1020 to form the lens 1000. The remainder of the gap 1030 may remain empty (or contain air) or may be filled with the same or different permeable oxygen and transparent material.

Once formed, the lens 1000 includes a lens body formed by the two layers 1010 and 1020 and the gap. The lens body, in turn, contains a transparent optical zone and a periphery. The periphery includes at least the area where the outer peripheries of the two layers 1010 and 1020 are mated. In an example, the light source for phototherapy is disposed within the gap 1030 within, for example, the portion of the gap 1030 corresponding to the transparent optical zone.

Generally, the first layer 1010 (e.g., the first lens) has a first curvature and the second layer 1020 (e.g., the second lens) has a second curvature different from the first curvature. Here, the curvatures can follow similar geometry, except that they may have a different bend radius. Outer peripheries of the first layer 1010 and the second layer 1020 mate at the periphery of the lens body. The gap 1030 is defined based on the first curvature and the second curvature. For instance, the gap is uniformly distributed around the lens body. In an example, each of the first layer 1010 and the second layer 1020 has a thickness between 10 and 100 µm. The gap separates the first layer 1010 and the second layer 1020 by starting at a significantly small separation at the mating area and increasing (e.g., linearly or in a parabolic manner) to achieve a maximum separation between the centers of the first layer 1010 and the second layer 1020. The maximum separation is in the range between 100 µm and 1 mm. The two layers 1010 and 1020 can be made of the same type of material, such as a rigid gas permeable (RGP) material.

In an illustration, two lenses (e.g., the two layers 1010 and 1020) are produced with geometry such that, when mated to one another, they produce a void space between them (e.g., the gap 1030). Within this void space the desired components to be encapsulated can be placed and affixed. The two lenses can then be affixed to each other along the mating interface (e.g. by means of a glue and/or bonding process) to create a sealed compartment between them. The outer seam of the composite lens can be ground/polished to achieve a seamless interface. The inner void can be air filled or may be filled with a material of suitably high oxygen permeability (e.g. perfluorocarbon, silicone). Filling the inner void with a material may help to improve the structural properties of the lens and/or improve the protection of the encapsulated components. Since the oxygen permeability of the inner void can be made sufficiently large (e.g. air, high oxygen permeability material) then the total oxygen permeability of the lens is dominated by the top and bottom lenses. One can select top and bottom lens material and thickness such that the total oxygen permeability of the lens is suitably high. Furthermore, since many of the components that may be encapsulated have low oxygen permeability they would pose a barrier were they to be encapsulated directly in the bulk material of the lens. However, since they are instead within a compartment of high oxygen permeability material, the oxygen is able to permeate around them and achieve a higher degree of uniformity on the inner face of the bottom lens. This maximizes oxygen transfer through the composite lens.

In another illustration, prior to forming the composite lens, low oxygen permeable components (e.g., light source, power source, controller, transceiver, sensors, electrodes, etc.) are fully or partially encapsulates with a high oxygen permeability material prior to encapsulation of these components into the composite lens. This provides a low resistance path for oxygen to permeate around the low oxygen permeability components, thus reducing the impact of the components on the overall oxygen permeability of the lens system.

Figure 11:
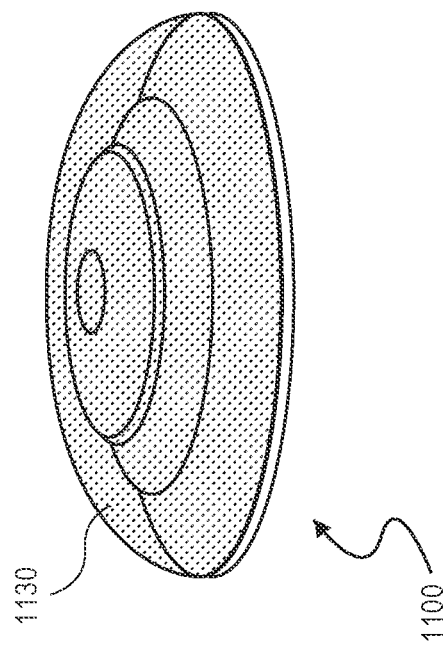
FIG. 11 illustrates another example of an assembly of a lens configurable as a phototherapy lens, according to embodiments of the present disclosure.
Figure 11:
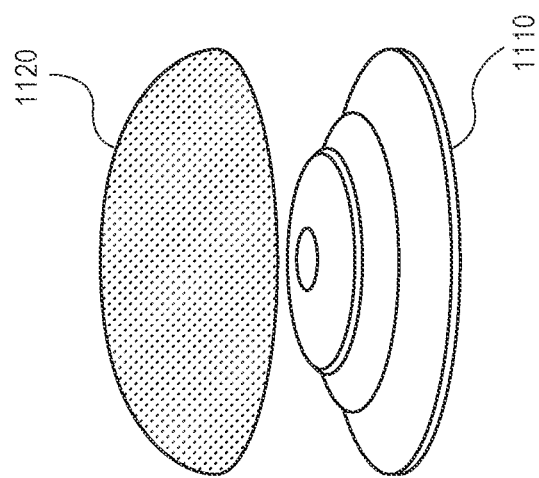

FIG. 11 illustrates another example of an assembly of a lens configurable as a phototherapy lens, according to embodiments of the present disclosure. The lens 1100 can be a phototherapeutic contact lens, such as the phototherapeutic contact lens 800 of FIG. 8, or a phototherapeutic intraocular lens, such as the phototherapeutic intraocular lens 900 of FIG. 9. Generally, the lens 1100 includes multiple lens layers and one or more gaps between the layers. Each layer may represent a lens on its own and can be designed for specific optical properties. Each gap is designed as a space where phototherapy-related components of the lens 1100 (e.g., light source, power source, controller, transceiver, sensors, electrodes, etc.) can be contained, and where this space is highly permeable to oxygen such that the oxygen can flow properly through the lens 1100 to the user eye or retina.

As illustrated in FIG. 11, the lens 1100 includes two lens layers and a gap 1130 (although a larger number of layers and/or gaps is possible). A first lens layer 1110 is a first lens and would be in contact with the user eye. Accordingly, this layer 1110 may be referred to as a contact lens. A second layer 1120 is a second lens, would not be in contact with the user eye, and would be positioned away from the user eye based on the gap 1130. For instance, this second layer 1120 is a vision-correction lens. The phototherapy-related components can be disposed within the gap 1130. Air, or other highly permeable oxygen and transparent material can fill the remainder of the gap 1130. Various permeable oxygen and transparent materials are possible including, for instance, perfluorocarbon, silicone, Vycor 7930 (a VYCOR material available from Corning, Inc. of New York, U.S.A.) and other nano-porous glasses. In this way, when the lens 1100 is worn by the user, oxygen flows from the surrounding physical environment into the gap 1130 through the second layer 1120 and out from the gap 1130 into the user eye through the first layer 1110.

In addition, prior to forming the lens 1100, any or all of the phototherapy-related components (e.g., light source, power source, controller, transceiver, sensors, electrodes, etc.) can be coated with or dipped in a permeable oxygen and transparent material, then placed in the gap 1130 prior to mating the first and second layers 1110 and 1120 to form the lens 1100. The remainder of the gap 1130 may remain empty (or contain air) or may be filled with the same or different permeable oxygen and transparent material.

Once formed, the lens 1100 includes a lens body formed by the two layers 1110 and 1120 and the gap. The lens body, in turn, contains a transparent optical zone and a periphery. The periphery includes at least the area where the outer peripheries of the two layers 1110 and 1120 are mated. In an example, the light source for phototherapy is disposed within the gap 1130 within, for example, the portion of the gap 1130 corresponding to the transparent optical zone.

Generally, the first layer 1110 (e.g., the first lens) has a first curvature and the second layer 1120 (e.g., the second lens) has a second curvature different from the first curvature. Here, the curvatures can have different geometries (e.g., one having a multi-step dome curvature, and one having a one dome curvature). The gap 1130 is defined based on the first curvature and the second curvature. For instance, the gap is uniformly distributed around the lens body. In an example, each of the first layer 1110 and the second layer 1120 has a thickness between 10 and 100 µm. The gap separates the first layer 1110 and the second layer 1120 by starting at a significantly small separation at the mating area and reaching a maximum separation in the range between 110 μm and 1 mm. The two layers 1110 and 1120 can be made of different types of materials. For instance, the first layer 1110 is made out of a rigid gas permeable (RGP) material, whereas the second layer 1120 is made out of silicone.

In an illustration, it may be advantageous to produce a composite lens composed of a bottom lens (e.g., the first layer 1110) with suitable properties for contact with the cornea bonded to an upper lens (e.g., the second layer 1120) composed of a higher oxygen permeability material that encapsulates system components. The benefits of this composite lens include, for instance, minimizing the used amount of lower oxygen permeability material for the bottom lens while maintaining suitable properties for corneal contact. For example, RGP materials have been developed for overnight contact lenses and have suitable properties for contact with the cornea. However, the oxygen permeability of these materials is significantly lower than materials like silicone. Conversely, silicone has been shown to have exceptionally high oxygen permeability; however, it is not ideal for contact with the cornea due to its tendency tighten and poor surface wettability. By encapsulating components in a high oxygen permeable layer (e.g. silicone), oxygen can be diffused around lower permeability components, and since this layer is composed of high oxygen permeable material it can encapsulate relatively thick components while minimally impacting overall oxygen permeability of the composite lens compared to directly encapsulating the components in the rigid RGP material that composes the bottom of the lens.

In a further illustration, the encapsulated components can be coated with or dipped in highly oxygen material prior to placement in or formation of the gap 1130.

The production of a composite lens utilizing the above techniques makes the integration of other lens technologies simple. In particular, one can utilize an orthokeratology lens as the bottom lens and then bond the encapsulating layer to it to produce a composite lens that combines the vision correction ability of the orthokeratology lens with the ability of the encapsulated system (e.g., phototherapy).

Specifically, there is high utility in the novel combination of technologies for present disease treatment with technologies for chronic disease treatment or prevention. The combination of orthokeratology (e.g., vision correction) with phototherapy (e.g., hypoxic eye disease treatment/prevention) is one example of this novel combination. The novel combination can also improve user compliance since users are incentivized to utilize therapy to treat the immediate problem of poor focus, but in doing so gain the benefits of the phototherapy to treat/prevent the slower acting hypoxic eye disease (e.g., diabetic retinopathy, macular edema, age-associated macular degeneration, etc.). This combination can solve the problem of low compliance observed in nearly all preventative therapies or treatments for chronic diseases, which occur because the future benefits of the present efforts are not seen and thus motivation for continuing with the regimen diminishes.

The phototherapy effectiveness can be further increased by using an agent that dilates the pupil during sleep or over time. Generally, the pupil constricts during sleep and with age. Since light entering the eye passes through the pupil, a larger diameter of the pupil can result in a more effective phototherapy. Two muscles control the size of the pupil: the iris sphincter muscle (constricts pupil under parasympathetic tone) and the iris dilator muscle (dilates pupil under sympathetic tone). The combination of reduced inhibition of the oculomotor nucleus (parasympathetic) and reduced sympathetic tone (e.g., during sleep and drowsiness) leads to pupil constriction.

Through pharmacological intervention it is possible to overcome the sleep-induced miosis. Parasympatholytics, such as anticholinergic mydriatics (e.g. Phenylephrine, Atropine, Tropicamide, Cyclopentolate, Oxyphenonium, Hyoscyamine, Epinephrine, Scopolamine, Yohimbine, Hydroxyamphetamine), are a class of compounds that block parasympathetic activity and prevent constriction of the ciliary muscle leading to pupil dilation. Sympathomimetics (e.g. phenylephrine, 4-hydroxyamphetamine) are compounds that act as agonists to the sympathetic nervous system, inducing contraction of the iris dilator muscle and thereby pupil dilation. The use of these compounds separately or in conjunction provides a means of dilating the pupil to improve the phototherapeutic dose transmitted through the pupil unto the retina. Care should be taken to ensure complications are managed appropriately (e.g. elevated intraocular pressure is a known side-effect). Mydriatics may be contraindicated for some patients.

Accordingly, in an embodiment of the present disclosure, a phototherapy kit is provided. The phototherapy kit includes at least one phototherapy eye device and at least a pupil constriction preventing agent. The phototherapy eye device can be any of the wearable phototherapy eye device 110 of FIG. 1, the wearable phototherapy eye device 200 of FIG. 2, the wearable phototherapy eye device 300 of FIG. 3, the phototherapy lens 710 of FIG. 7, the phototherapeutic contact lens 800 or FIG. 8, or the phototherapeutic intraocular lens 900 of FIG. 9. The pupil constriction preventing agent can be a compound, such as a medicine solution, that includes any or a combination of parasympatholytics, anticholinergic mydriatics, such as Phenylephrine, Atropine, Tropicamide, Cyclopentolate, Oxyphenonium, Hyoscyamine, Epinephrine, Scopolamine, Yohimbine, and/or Hydroxyamphetamine, and sympathomimetics, such as phenylephrine and/or 4-hydroxyamphetamine. In an example, the pupil constriction preventing agent is provided in the kit as an eye drop solution packaged in a container (e.g., a bottle that contains the pupil constriction preventing agent and a medicine dropper such as a Pasteur pipette, or a syringe type eye drops container that includes the pupil constriction preventing agent).

In a further embodiment, a method of phototherapy treatment is provided. This method includes obtaining the phototherapy kit by a subject, receiving the pupil constriction preventing agent as at least an eye drop to the eye of the subject, wearing the phototherapy eye device over at least one eye of the subject, and repeating the receiving of the pupil constriction preventing agent and/or wearing the phototherapy eye device over time. In addition, a method of prescribing a phototherapy treatment is provided. This method includes instructing, by a physician, a patient to obtain the phototherapy kit or to obtain the pupil constriction preventing agent and the phototherapy eye device, receive the pupil constriction preventing agent as at least an eye drop to the eye of the subject, wear the phototherapy eye device over at least one eye of the subject, and repeat the receiving of the pupil constriction preventing agent and/or wearing the phototherapy eye device over time.

While the foregoing has described what are considered to be the best mode and/or other examples, it is understood that various modifications may be made therein and that the subject matter disclosed herein may be implemented in various forms and examples, and that the teachings may be applied in numerous applications, only some of which have

What is claimed is:

1. A wearable phototherapy eye device comprising:
a facial housing having a user eye side;
a radioluminescent light source disposed in or on the facial housing configured to emit radioluminescent light towards or from the user eye side; and
a shutter comprising a low light transmissivity portion having transmissivity relative to the radioluminescent light below a transmissivity level, wherein the shutter is configured to vary an emission property of the radioluminescent light based on a relative position between the low light transmissivity portion and the radioluminescent light source.

2. The wearable phototherapy eye device of claim 1, wherein the light source comprises a cylindrical housing that has a transparent portion, wherein the shutter comprises a tubular housing that has an opaque portion corresponding to the low light transmissivity portion, wherein the cylindrical housing is disposed inside the tubular housing, and wherein the emission property is varied based on a rotational movement of at least one of the cylindrical housing or the tubular housing such that the relative position between the transparent portion and the opaque portion is changed.

3. The wearable phototherapy eye device of claim 1, wherein the light source comprises a prismatic housing that has a transparent portion, wherein the shutter comprises an enclosure that has an opaque portion corresponding to the low light transmissivity portion, and wherein the emission property is varied based on a translational movement of at least one of the prismatic housing relative to the enclosure or the enclosure relative to the prismatic housing such that the relative position between the transparent portion and the opaque portion is changed.

4. The wearable phototherapy eye device of claim 1, wherein the light source comprises a housing that has a first pattern of transparent gratings and opaque gratings, wherein the shutter comprises an enclosure that has a second pattern of transparent gratings and opaque gratings, and wherein the emission property is varied based on at least one of a translational movement or a rotational movement of at least one of the housing or the enclosure such that the relative position between the first pattern and the second pattern is changed.

5. The wearable phototherapy eye device of claim 1, wherein the light source comprises a cylindrical housing that has a transparent portion, wherein the shutter comprises a hemi-circular housing that has an opaque portion corresponding to the low light transmissivity portion, and wherein the emission property is varied based on a rotational movement of the hemi-circular housing relative to the cylindrical housing such that the relative position between the transparent portion and the opaque portion is changed.

6. The wearable phototherapy eye device of claim 1, wherein the shutter comprises a reservoir and a transparent channel that is positioned between the radioluminescent light source and the user eye side, wherein the reservoir comprises a ferrofluid, wherein the emission property is varied based on an amount of the ferrofluid in the transparent channel from the reservoir.

7. The wearable phototherapy eye device of claim 1, wherein the shutter comprises an optical waveguide that has an opaque gate, wherein the emission property is varied based on a movement of the opaque gate.

8. The wearable phototherapy eye device of claim 1, wherein the emission property is varied further based on a predetermined transfer function of the emitted light from the wearable phototherapy eye device to an eye retina.

9. The wearable phototherapy eye device of claim 8, further comprising a set of electrodes configured to measure an electrical response of the eye retina at different light emission levels, wherein the predetermined transfer function is defined based on the electrical response.

10. The wearable phototherapy eye device of claim 1, further comprising:
a receiving coil configured to induce electrical current based on a wireless power transmission from a transmission coil; and
a converter configured to convert the induced electrical current into a converted electrical current.

11. The wearable phototherapy eye device of claim 10, further comprising:
a controller electrically coupled with the shutter and configured to vary the relative position between the low light transmissivity portion and the radioluminescent light source; and
an energy storage electrically coupled with the converter and the controller and configured to supply power to the controller.

12. The wearable phototherapy eye device of claim 11, further comprising:
a set of sensors configured to measure data associated with at least one of a wear time of the wearable phototherapy eye device, a motion of the facial housing, or a user motion, wherein the relative position is varied by the controller based on the data.

13. The wearable phototherapy eye device of claim 12, further comprising:
a transceiver configured to transmit the data to a computing device and receive a setting of the emission property from the computing device, the setting received based on a determination by the computing device of a sleep phase in response to the data.

14. The wearable phototherapy eye device of claim 1, further comprising:
one or more light sensors configured to measure light reflected from an eye lid of a wearer of the device.

15. The wearable phototherapy eye device of claim 1, further comprising:
a coating of permeable oxygen and transparent material that envelops the housing, the light source, and the shutter.

16. The wearable phototherapy eye device of claim 1, wherein the radioluminescent light source comprises gaseous tritium.

17. The wearable phototherapy eye device of claim 1, wherein the radioluminescent light source comprises a radioisotope-based light source.

18. The wearable phototherapy eye device of claim 1, wherein the emission property of the radioluminescent light through the shutter is greater than $10^{12}$ photons/second/$cm^2$ on a retina of a wearer of the device to induce rod hyperpolarization.

19. The wearable phototherapy eye device of claim 1, further comprising:
a phosphor material coating of the light source to minimize visual side-effects of continuous phototherapy at wavelengths of cone cells.

20. The wearable phototherapy eye device of claim 1, further comprising:
at least one of an optical waveguide, a reflector, and a filter to direct the emitted radioluminescent light towards a retina of a wearer of the device.

* * * * *